United States Patent
Nishida et al.

(10) Patent No.: US 12,059,236 B2
(45) Date of Patent: Aug. 13, 2024

(54) BLOOD PRESSURE MEASUREMENT DEVICE

(71) Applicants: OMRON CORPORATION, Kyoto (JP); OMRON HEALTHCARE CO., LTD., Muko (JP)

(72) Inventors: Tomoyuki Nishida, Kyoto (JP); Takanori Nishioka, Kyoto (JP); Yoshihiko Sano, Kyoto (JP); Brian Brigham, Kyoto (JP); Takashi Ono, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/912,771

(22) Filed: Jun. 26, 2020

(65) Prior Publication Data
US 2020/0323446 A1 Oct. 15, 2020

Related U.S. Application Data

(63) Continuation of application No. PCT/JP2018/043759, filed on Nov. 28, 2018.

(30) Foreign Application Priority Data

Dec. 28, 2017 (JP) .................................. 2017-252899

(51) Int. Cl.
*A61B 5/022* (2006.01)
*A61B 5/00* (2006.01)
(Continued)

(52) U.S. Cl.
CPC ........ *A61B 5/02233* (2013.01); *A61B 5/0235* (2013.01); *A61B 5/681* (2013.01); *A61B 2562/0219* (2013.01)

(58) Field of Classification Search
CPC ... A61B 5/02233; A61B 5/0235; A61B 5/681; A61B 2562/0219; A61B 5/7475;
(Continued)

(56) References Cited

U.S. PATENT DOCUMENTS 4,860,761 A * 8/1989 Yamasawa ......... A61B 5/02255
600/499
6,336,901 B1 * 1/2002 Itonaga .................. A61B 5/681
600/499

(Continued)

FOREIGN PATENT DOCUMENTS

JP A 62-72315 * 4/1987
JP 2000-051165 A 2/2000
(Continued)

OTHER PUBLICATIONS

Google translation of WO 2014/102870 A1 (Year: 2014).*
(Continued)

*Primary Examiner* — Alex M Valvis
*Assistant Examiner* — Justin Xu
(74) *Attorney, Agent, or Firm* — Oliff PLC

(57) ABSTRACT

The blood pressure measurement device includes a bag-like cuff wound around the living body and inflated with a fluid supplied to its internal space, a supply device configured to supply the fluid into the cuff, and guides arranged on the living body side of the cuff and configured to create wrinkles in the cuff on the living body side in a direction intersecting the winding direction of the cuff, when the cuff is inflated to pressurize the living body.

2 Claims, 22 Drawing Sheets

(51) Int. Cl.
  *A61B 5/021*  (2006.01)
  *A61B 5/0235*  (2006.01)
  *G04G 21/02*  (2010.01)
  *A61B 5/0205*  (2006.01)
  *A61B 5/11*  (2006.01)

(58) Field of Classification Search
  CPC ............... A61B 5/6824; A61B 5/6831; A61B 2562/0247; A61B 5/0205; A61B 5/02225; A61B 5/02141; A61B 5/1118; A61B 5/742; A61B 5/022; G04G 21/025
  See application file for complete search history.

(56) References Cited

U.S. PATENT DOCUMENTS

| | | | | |
|---|---|---|---|---|
| 2009/0163823 | A1* | 6/2009 | Takahashi | A61B 5/6843 |
| | | | | 600/490 |
| 2009/0234381 | A1 | 9/2009 | Karo | |
| 2011/0112412 | A1* | 5/2011 | Sano | A61B 5/02233 |
| | | | | 600/499 |
| 2012/0150051 | A1* | 6/2012 | Kinsley | A61B 5/02233 |
| | | | | 600/499 |
| 2019/0099095 | A1* | 4/2019 | Zhang | A61B 5/6826 |

FOREIGN PATENT DOCUMENTS

| | | |
|---|---|---|
| JP | 2005-329162 A | 12/2005 |
| JP | 2007-175185 A | 7/2007 |
| JP | 2011-200607 A | 10/2011 |
| JP | 2013-192878 A | 9/2013 |
| WO | 2014/102870 A1 | 7/2014 |
| WO | 2014/102871 A1 | 7/2014 |

OTHER PUBLICATIONS

Jul. 2, 2020 Translation of International Preliminary Report on Patentability issued in International Patent Application No. PCT/JP2018/043759.

Feb. 12, 2019 International Search Report issued in International Patent Application No. PCT/JP2018/043759.

Jul. 20, 2021 Office Action issued in Japanese Patent Application No. 2017-252899.

* cited by examiner

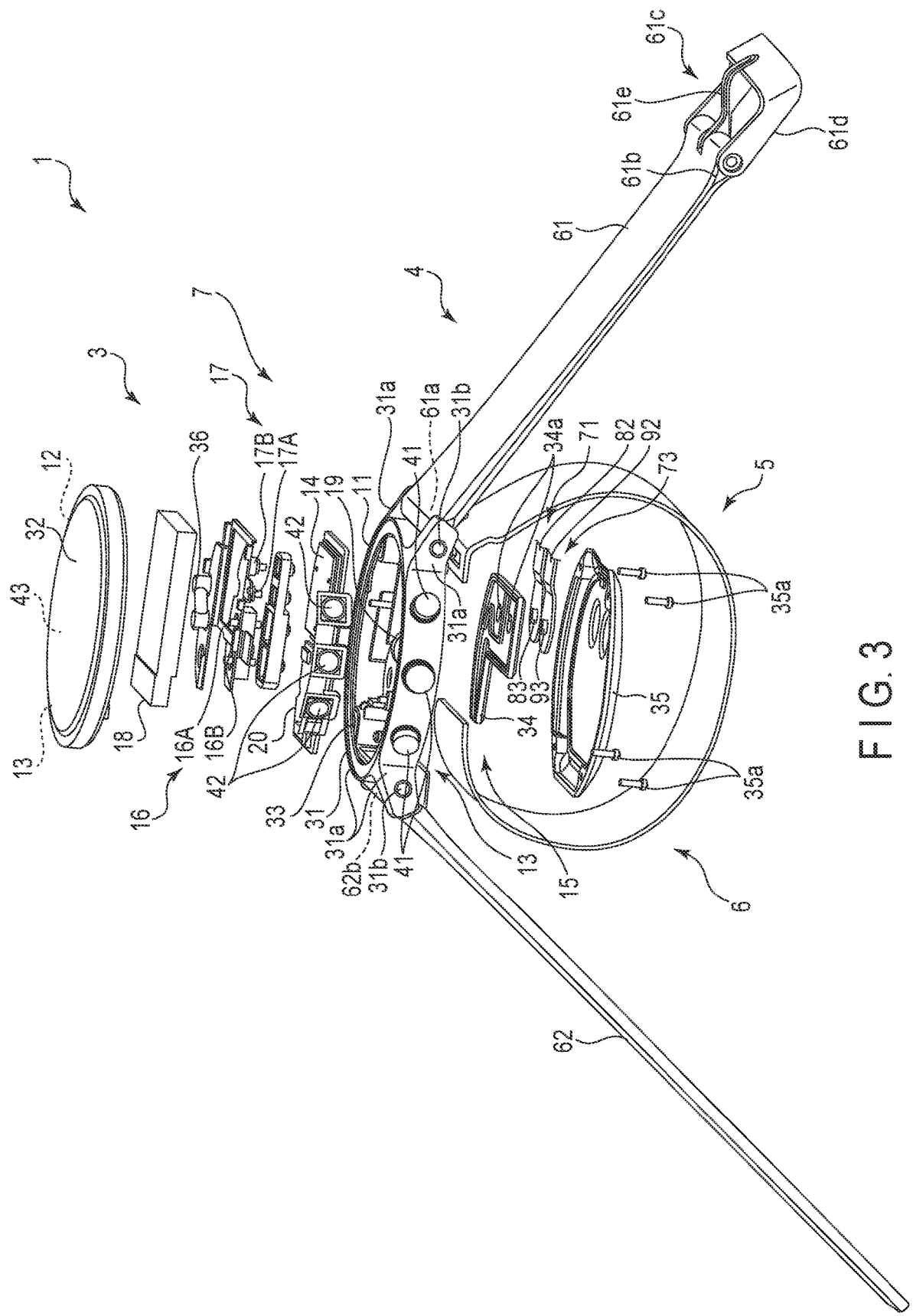
F I G. 3

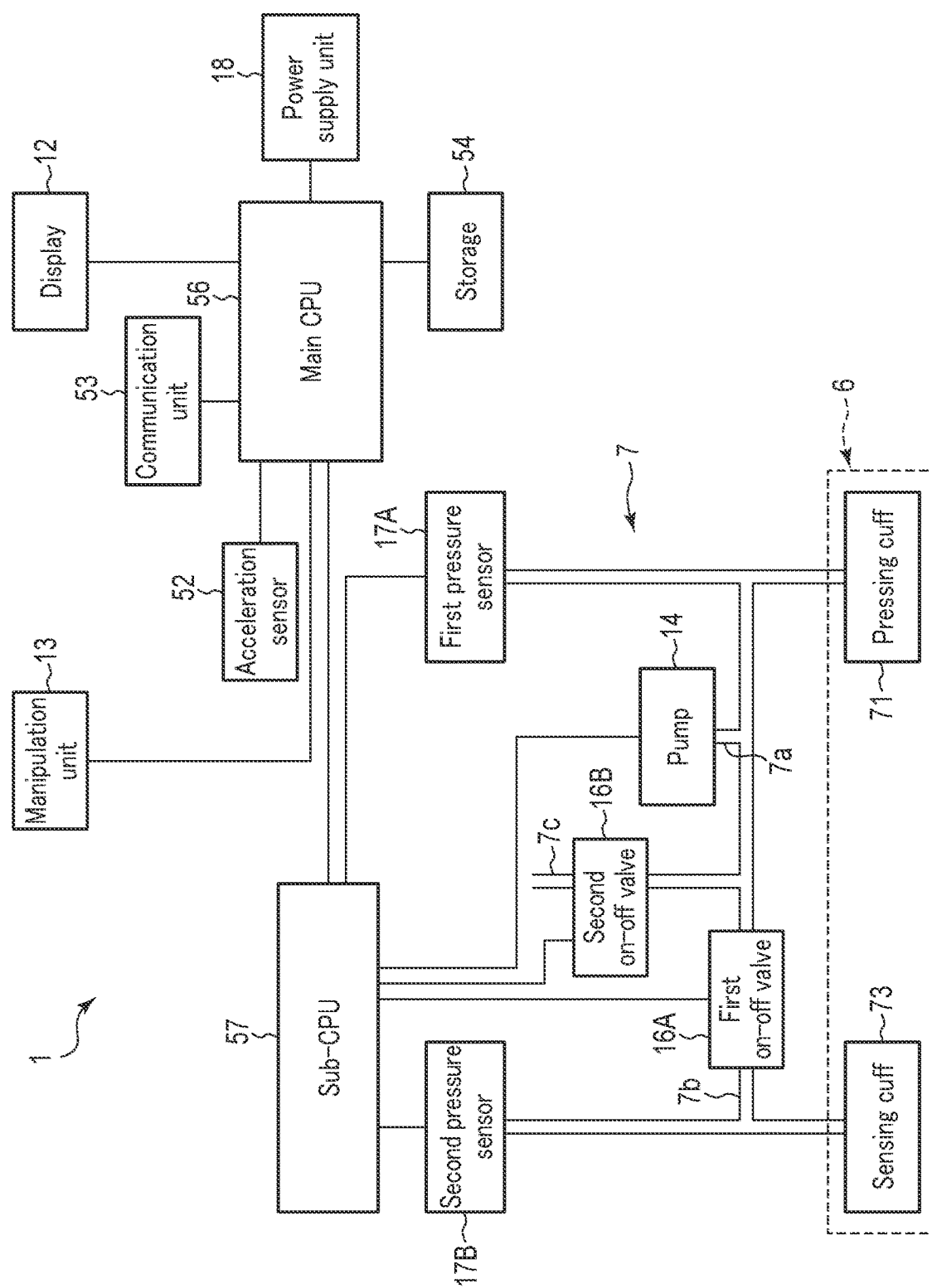
F I G. 4

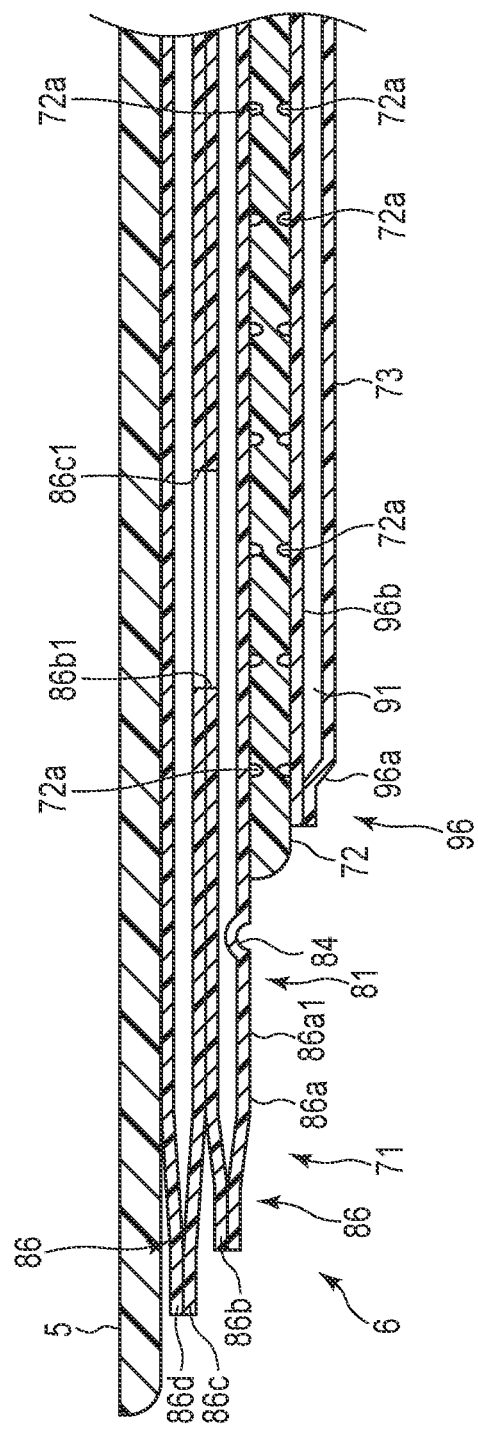
F I G. 10

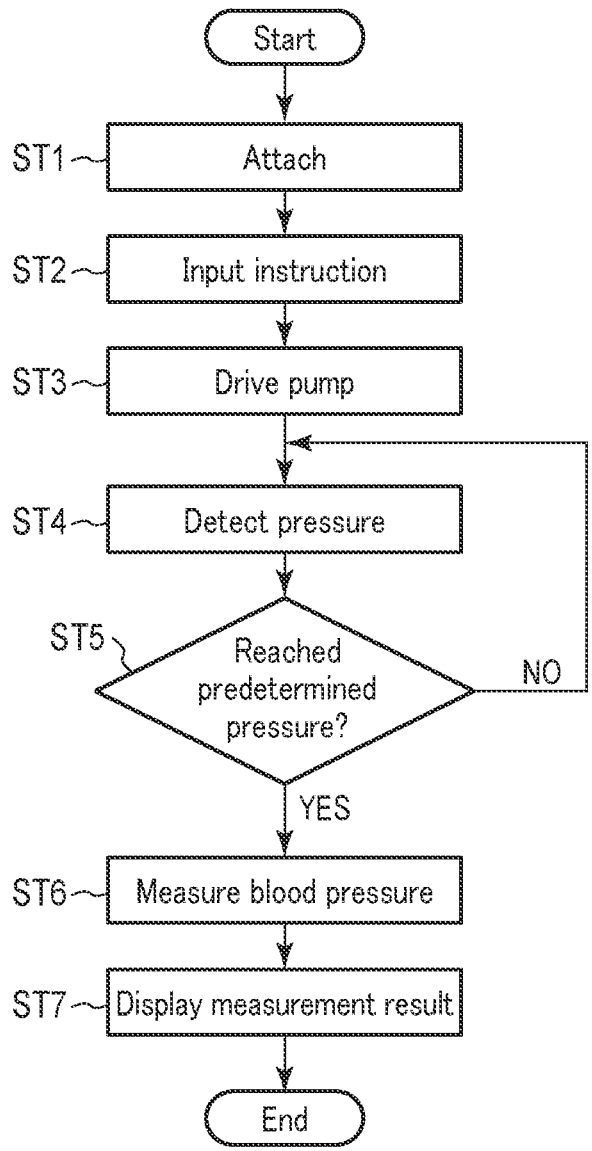
F I G. 14

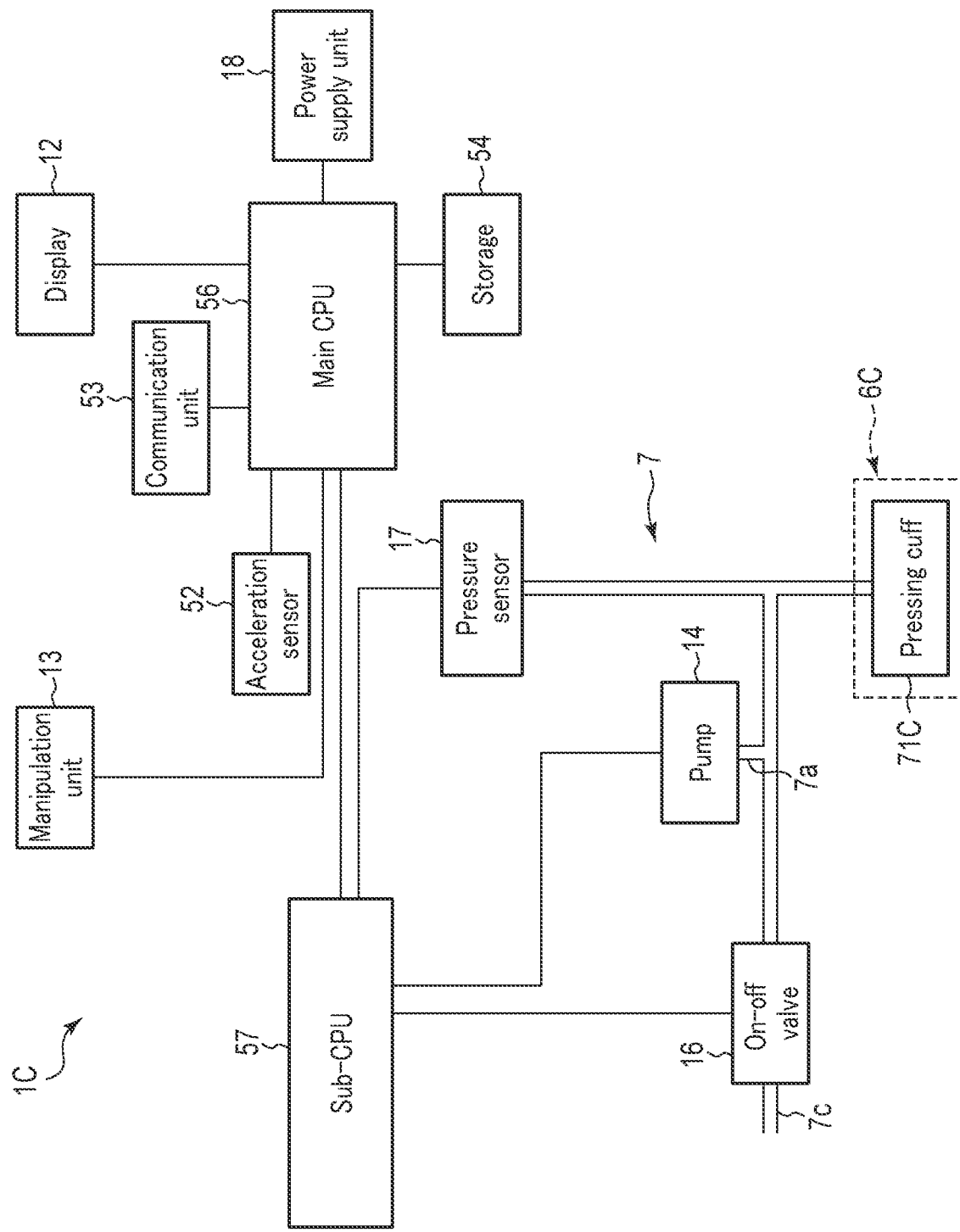
F I G. 24

BLOOD PRESSURE MEASUREMENT DEVICE

CROSS-REFERENCE TO RELATED APPLICATIONS

This is a Continuation Application of PCT application No. PCT/JP2018/043759, filed Nov. 28, 2018, which was published under PCT Article 21(2) in Japanese.

This application is based upon and claims the benefit of priority from Japanese Patent Application No. 2017-252899, filed Dec. 28, 2017, the entire contents of which are incorporated herein by reference.

BACKGROUND

Field

The present invention relates to a blood pressure measurement device for the measurement of blood pressure.

Description of the Related Art

Recently, a blood pressure measurement device have been employed not only in medical facilities but also at home as a means for checking health conditions. Blood pressure may be measured by winding a cuff of a blood pressure measurement device around an upper arm or wrist of a living body, inflating and contracting the cuff, detecting the pressure of the cuff with the pressure sensor, and thereby detecting the vibration of the artery wall.

When the cuff is wound around the living body and inflated, a difference appears between the lengths of the outer peripheral surface and inner peripheral surface of the inflated cuff, wrinkling the living-body side of the cuff. The wrinkles in the cuff may vary in their number, positions and depths, depending on the circumference and shape of the living body around which the cuff is wound, the winding manner of the cuff, and the like.

Depending on the number, positions and depths of the wrinkles in the cuff, a division inside the cuff may be created, resulting in a loss of inflating pressure. This may adversely affect the measurement result of the blood pressure such as decreasing the accuracy of the blood pressure measurement and causing variations in the measurement result.

A cuff for a blood pressure measurement device capable of suppressing wrinkling in a bag-like cover has been known, as disclosed in Jpn. Pat. Appln. KOKAI Publication No. 2007-175185. In such a blood pressure measurement device cuff, a curler is included in the bag-like cover that contains an air bag, and this curler has a large curvature portion and a small curvature portion in the winding direction so that the cuff can fit the measurement target site. When the air bag is in an uninflated state, a portion of an inner cover component corresponding to the large curvature portion of the curler is stretched in the width direction so that wrinkling can be suppressed. This blood pressure measurement device cuff may demonstrate such an effect through a configuration in which the widths of the inner cover component and outer cover component that are seamed together in the portion of the bag-like cover corresponding to the large curvature portion of the curler differ from the seamed widths in other portions.

SUMMARY

In general, in addition to the above-mentioned configuration of the blood pressure measurement device cuff having an air bag and a curler in a bag-like cover, a configuration of a cuff to which a fluid is supplied and which is brought into contact with the living body and a configuration in which a plurality of air bags are stacked have also been known. For such cuffs of various types, a technique for suppression of wrinkles adversely affecting the measurement result of the blood pressure, is demanded.

According to one aspect of the invention, a blood pressure measurement device is provided, which includes: a bag-like cuff configured to be wound around a living body and inflated with a fluid supplied into the internal space thereof; a supply device configured to supply the fluid into the cuff; guides arranged on the living body side of the cuff, and configured to create wrinkles in the cuff on the living body side in a direction intersecting the winding direction of the cuff when the cuff is inflated to pressurize the living body.

Here, the fluid may include liquid and air. Wrinkles are creases that are created in the inner peripheral surface of the cuff so that part of the inner peripheral surface can move toward the outer peripheral surface side when the bag-like cuff wound around the living body is inflated, and a difference appears between the lengths of the outer peripheral surface and the inner peripheral surface of the cuff (i.e., inner/outer peripheral difference).

The cuff is wound around the upper arm or wrist of the living body to measure the blood pressure, and inflated when a fluid is supplied thereto. The cuff may include a pressing cuff and sensing cuff provided in a blood pressure measurement device that measures the blood pressure around the wrist, and a cuff provided in a blood pressure measurement device that measures the blood pressure around the upper arm. The cuff may be a bag-like structure such as an air bag that constitutes a pressing cuff.

In addition, the supply device is the main body of the blood pressure measurement device that includes a pump and a flow passage.

According to this aspect of the invention, when the cuff is wound around the living body and inflated, an inner/outer peripheral difference creates wrinkles in the inner peripheral surface along the guides, and the positions and depths of wrinkles can be controlled in this manner.

The wrinkles created in the inner peripheral surface of the cuff may divide the internal space of the cuff, depending on the positions and depths of the wrinkles. The wrinkles may adversely affect the blood pressure measurement result, such as by reducing the accuracy of the measured blood pressure values, due to variation in the pressure of the cuff pressurizing the living body. However, with the arrangement of guides, the positions of wrinkles that appear in the inner peripheral surface of the cuff can be controlled so that variation can be suppressed in the position and depth of wrinkles created in the inner peripheral surface of the cuff, which may be caused due to the difference in individual living bodies and the cuff usage conditions at the time of inflation. According to this aspect, the blood pressure measurement device can stably pressurize the living body with the cuff, and thus variation in the measured blood pressure values can be avoided, and accuracy in the blood pressure measurement result can be improved.

The blood pressure measurement device according to the above aspect of the invention can be provided, in which the guides are grooves arranged in the outer surface of the cuff.

According to this aspect of the invention, with the guides being grooves, the wrinkles can be controlled with a simple configuration, without increasing the thickness of the cuff.

The blood pressure measurement device according to the above aspect of the invention can be provided, in which the guides are arranged in positions of the cuff that do not face the artery of the living body.

According to this aspect of the invention, the guides are arranged at the positions of the cuff that do not face the artery of the living body, and therefore appearance of wrinkles can be suppressed at the positions of the cuff that face the artery. Even if wrinkles are created at such positions when the cuff is inflated, these wrinkles would appear with a depth smaller than that of the wrinkles created by the guides.

The blood pressure measurement device according to the above aspect of the invention can be provided, in which the guides are provided at regular intervals.

According to this aspect of the invention, by creating wrinkles at regular intervals in the inner peripheral surface of the cuff, the wrinkles have substantially the same depth, thus preventing some of the wrinkles from having a larger depth than others.

The blood pressure measurement device according to the above aspect of the invention can be provided, in which the guides create wrinkles in a direction perpendicular to the winding direction of the cuff.

According to this aspect of the invention, with the wrinkles created in the direction perpendicular to the winding direction of the cuff around the living body, the wrinkles in the cuff would not overlap with one another.

The blood pressure measurement device according to the above aspect of the invention can be provided, which includes a back plate arranged on the living body side of the cuff and extending in the circumferential direction of the living body; a bag-like sensing cuff arranged on the living body side of the back plate, arranged in the area of the artery of the wrist when the cuff is wound around the living body, and inflated when fluid is supplied to the internal space thereof; a pump that supplies the fluid to the cuff and the sensing cuff; a main body in which the pump is held; and a strap arranged on the main body and attached along the circumferential direction of the wrist.

The measurement target site represents an area of the living body where the artery runs and where the blood pressure can be measured. This may be the wrist, upper arm or ankle.

According to this aspect, a wearable blood pressure measurement device that can be attached around the wrist can control wrinkles even if the cuff has a relatively small width. That is, the cuff of the blood pressure measurement device that is attached to the wrist has a small width, and therefore tends to be significantly influenced by the wrinkles in the cuff, resulting in, for example, reduction in the accuracy of the blood pressure measurement. With the control of wrinkles, however, the blood pressure measurement device can prevent the blood pressure values from varying because of the wrinkles, and the accuracy of the blood pressure measurement result can be improved.

The present invention offers a blood pressure measurement device that can improve the accuracy of the measurement result of the blood pressure by suppressing the appearance of wrinkling.

BRIEF DESCRIPTION OF THE DRAWINGS

FIG. 3 is an exploded view showing the configuration of the blood pressure measurement device.

FIG. 4 is a block diagram showing the configuration of the blood pressure measurement device.

FIG. 10 is a cross-sectional view showing the configuration of the curler and cuff structure of the blood pressure measurement device.

FIG. 14 is a flowchart showing an exemplary use of the blood pressure measurement device.

FIG. 24 is a block diagram showing the configuration of the blood pressure measurement device.

DETAILED DESCRIPTION

First Embodiment

An example of a blood pressure measurement device 1 according to the first embodiment of the present invention will be described with reference to FIGS. 1 to 12.

Figure 1:
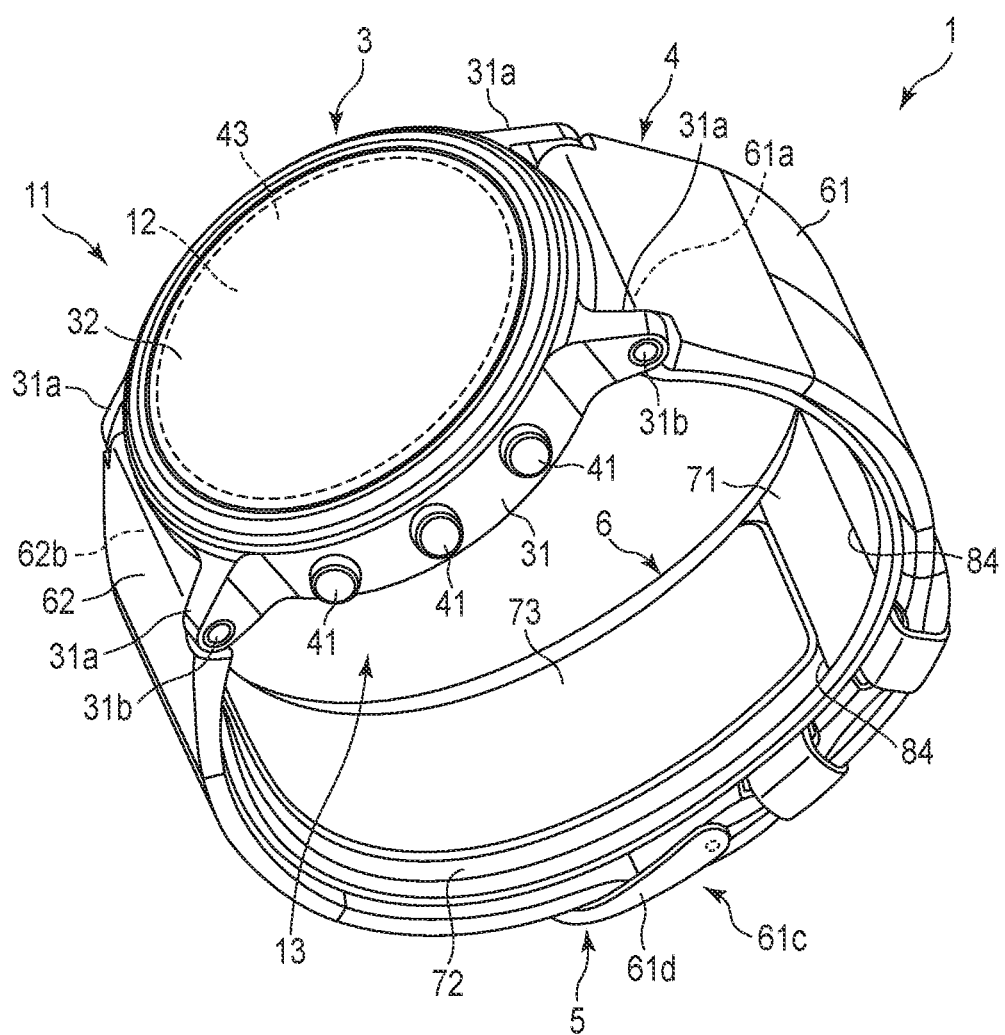
FIG. 1 is a perspective view showing the configuration of a blood pressure measurement device according to the first embodiment of the present invention.

FIG. 1 is a perspective view of the configuration of the blood pressure measurement device 1 according to the first embodiment of the present invention with a strap 4 buckled.

Figure 2:
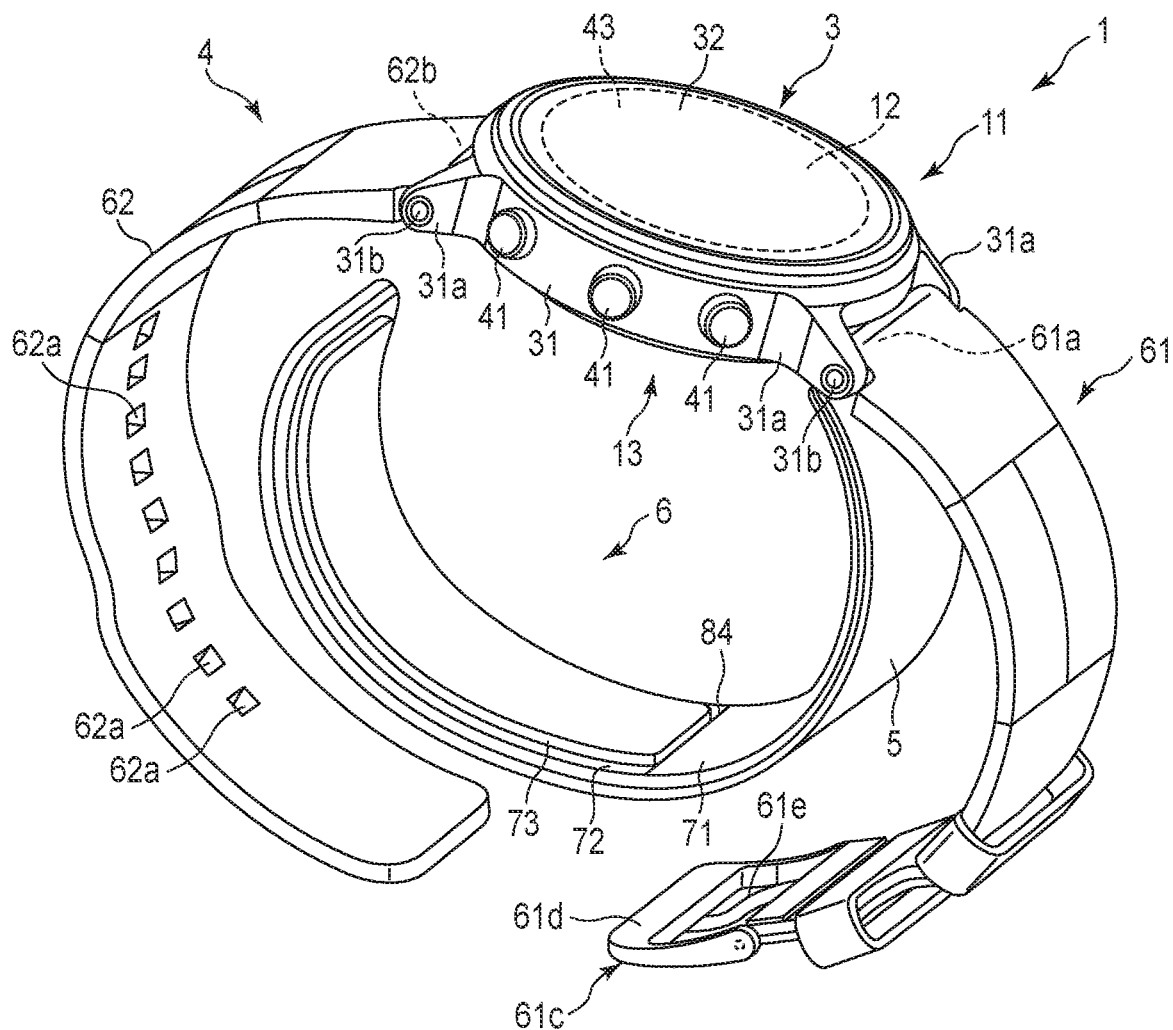
FIG. 2 is a perspective view showing the configuration of the blood pressure measurement device.
Figure 5:
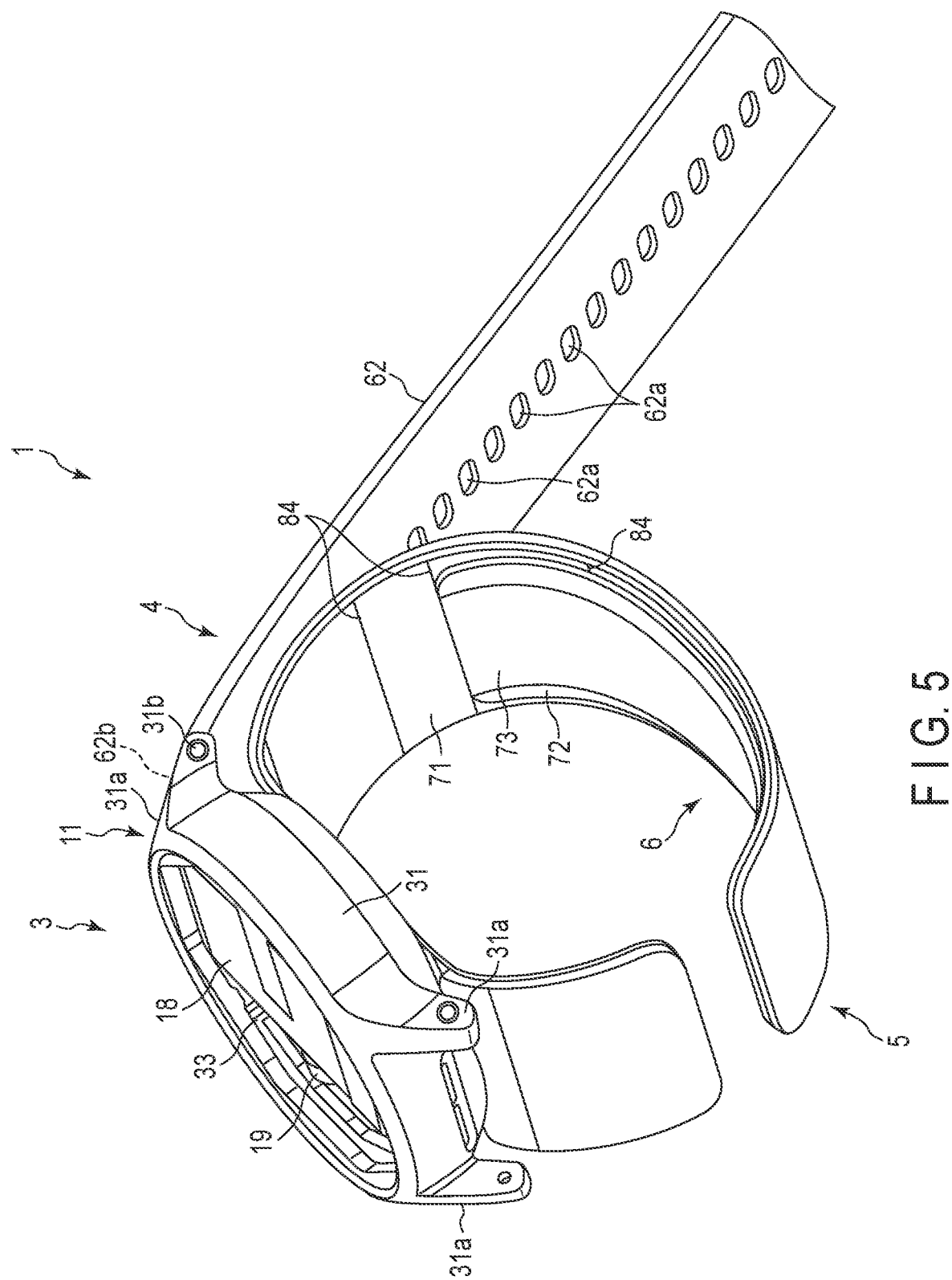
FIG. 5 is a perspective view showing another configuration of the blood pressure measurement device.
Figure 6:
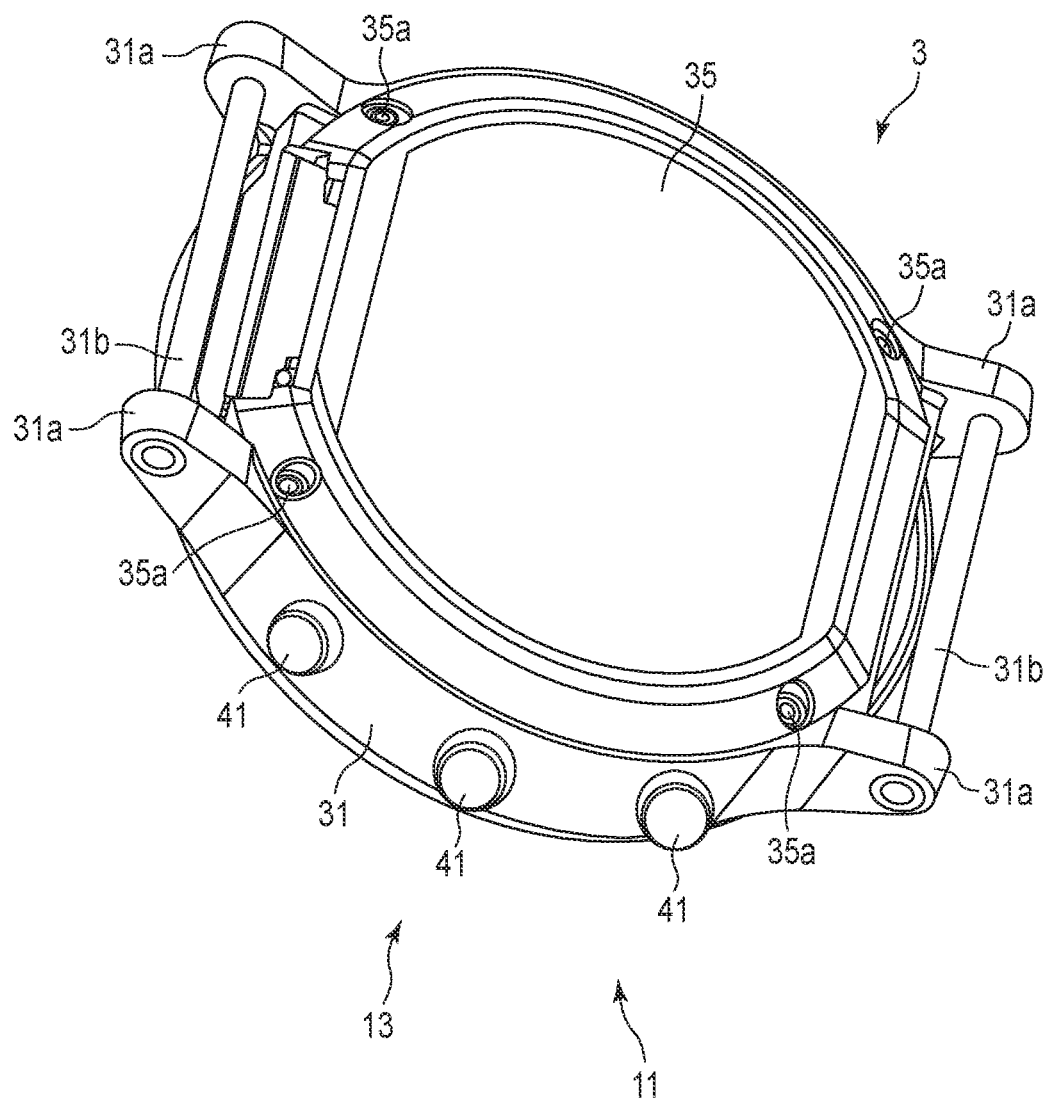
FIG. 6 is a perspective view showing the configuration of the main body of the blood pressure measurement device.
Figure 7:
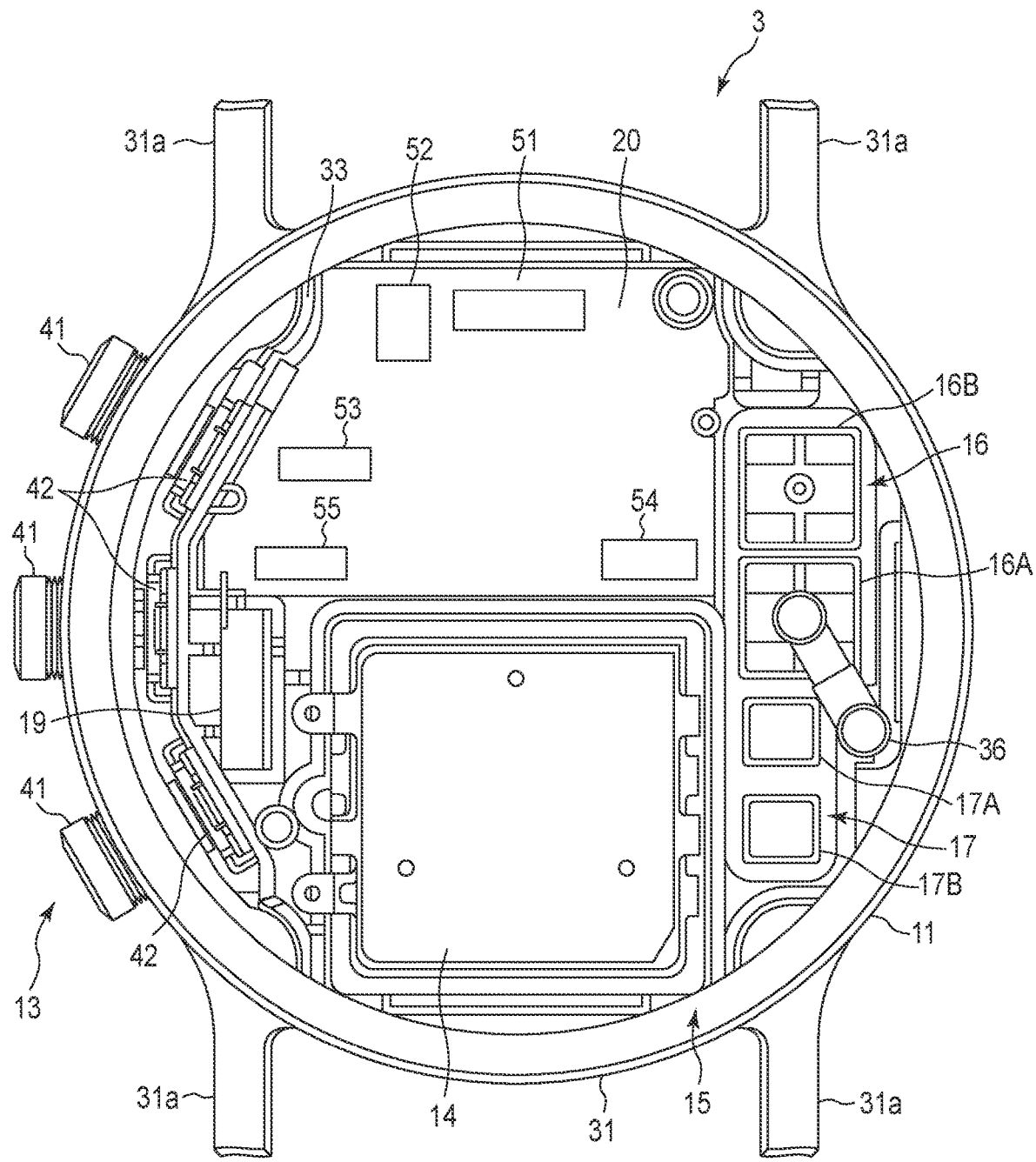
FIG. 7 is a plan view showing the internal configuration of the main body.
Figure 8:
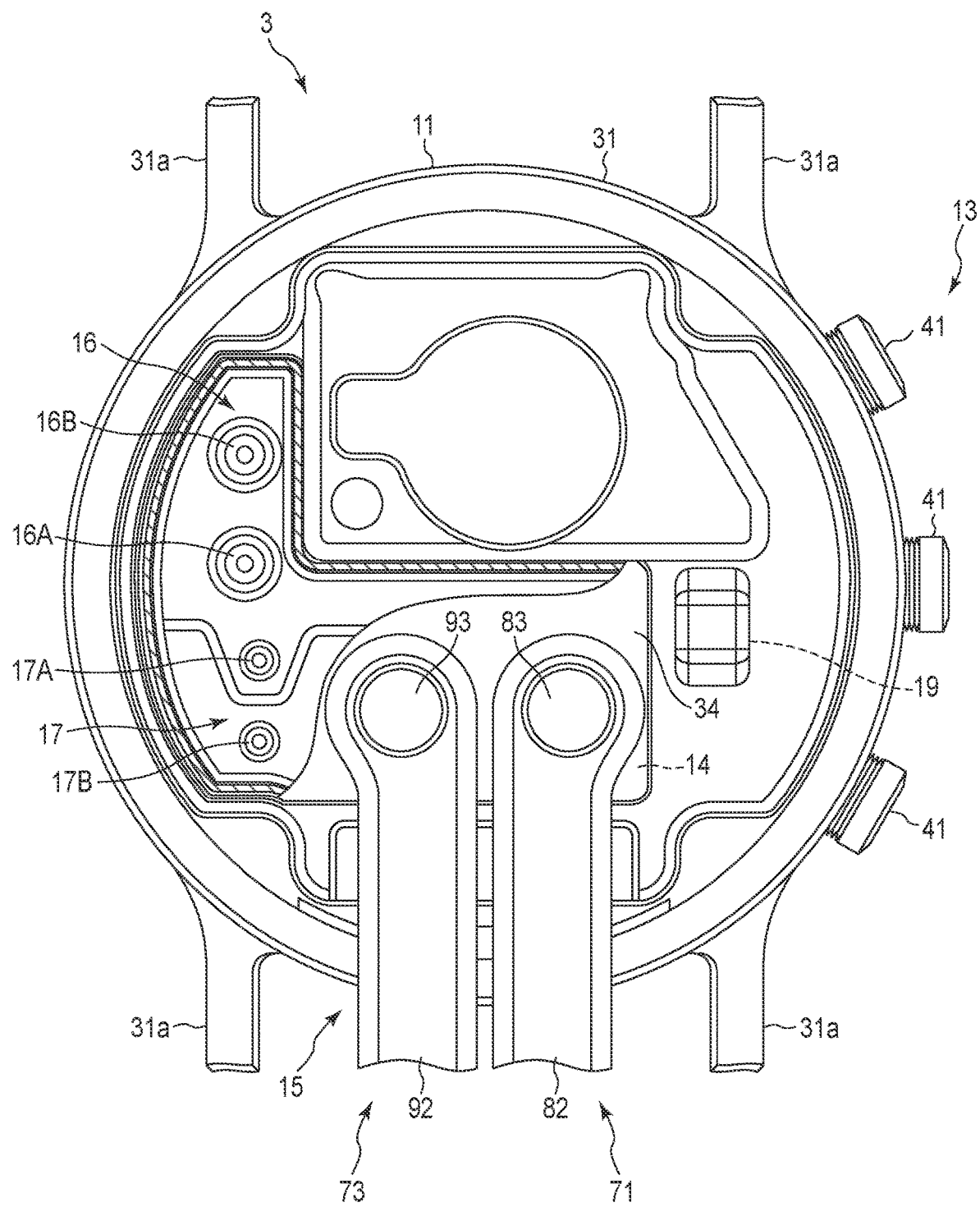
FIG. 8 is a plan view showing the internal configuration of the main body.
Figure 9:
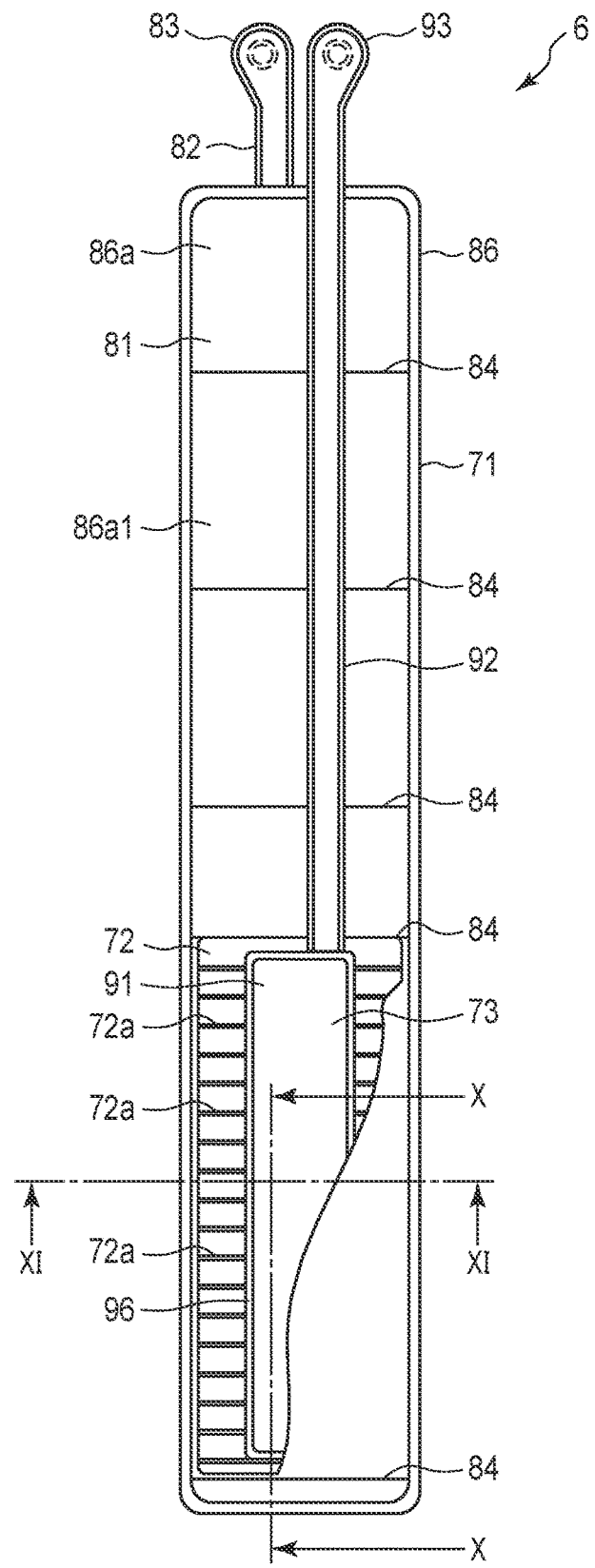
FIG. 9 is a plan view showing the configuration of the cuff structure of the blood pressure measurement device.

FIG. 2 is a perspective view of the configuration of the blood pressure measurement device 1 with the strap 4 unbuckled. FIG. 3 is an exploded view of the configuration of the blood pressure measurement device 1. FIG. 4 is a block diagram of the configuration of the blood pressure measurement device 1. FIG. 5 is a perspective view of another configuration of the blood pressure measurement device 1. FIG. 6 is a perspective view of the configuration of the main body 3 of the blood pressure measurement device 1 viewed from the back cover 35 side. FIGS. 7 and 8 are plan views of the internal configuration of the main body 3 when viewed from the windshield 32 side and the back cover 35 side, respectively. FIG. 9 is a plan view of the configuration of the cuff structure 6 of the blood pressure measurement device 1 when viewed from the sensing cuff 73 side.

Figure 11:
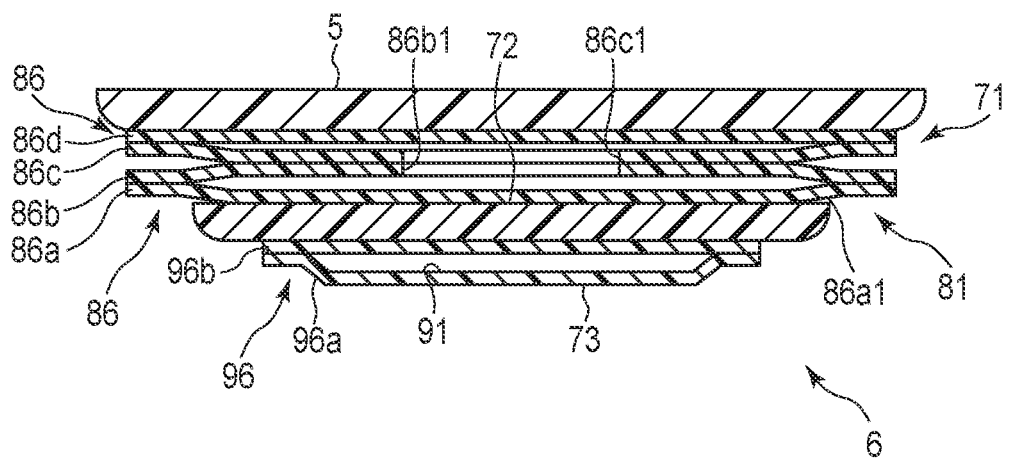
FIG. 11 is a cross-sectional view of the configuration of the curler and cuff structure.
Figure 12:
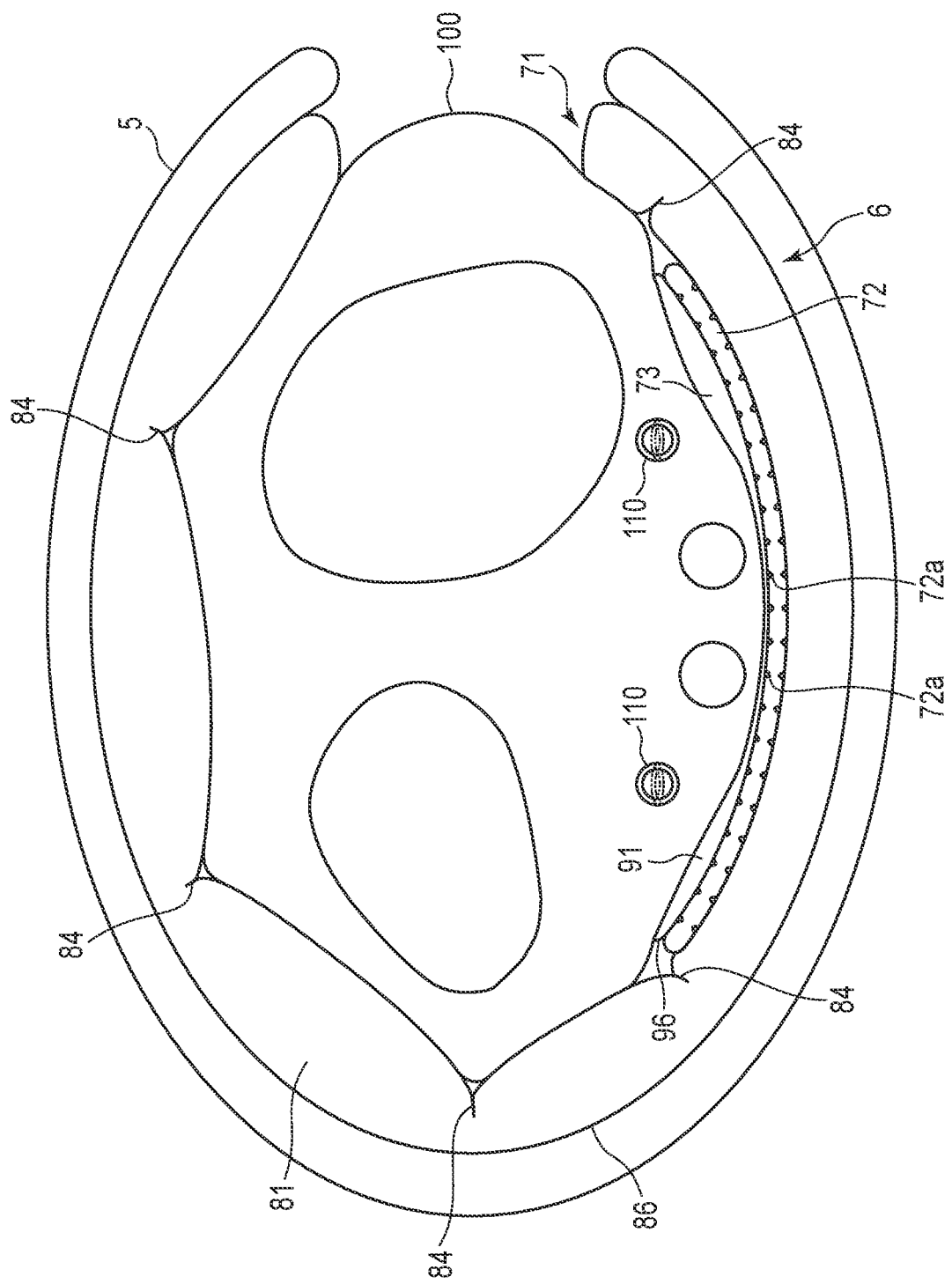
FIG. 12 is a side view schematically showing the configuration of the pressing cuff of the cuff structure when inflated.
Figure 13:
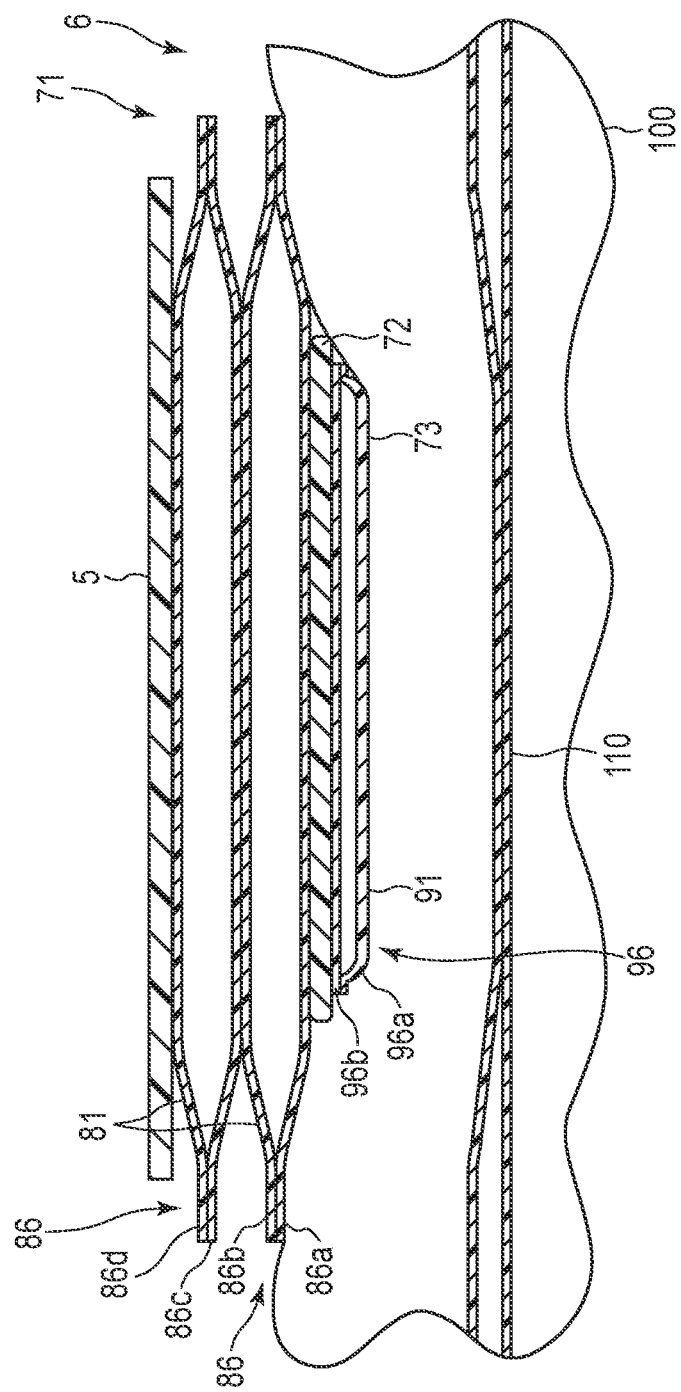
FIG. 13 is a cross-sectional view schematically showing the configuration of the pressing cuff of the cuff structure when inflated.

FIG. 10 is a cross-sectional view schematically showing the configuration of the curler 5 and cuff structure 6 of the blood pressure measurement device 1 along the line X-X in FIG. 9. FIG. 11 is a cross-sectional view of the configuration of the curler 5 and the cuff structure 6 along the line XI-XI in FIG. 9. FIGS. 12 and 13 are a side view and cross-sectional view schematically illustrating the pressing cuff 71 and sensing cuff 73 of the cuff structure 6 when inflated. In FIG. 10, the curler 5 and cuff structure 6 are linearly illustrated for the simplicity of explanation; however, in the actual arrangement in the blood pressure measurement device 1, they have a bent form.

The blood pressure measurement device 1 is an electronic blood pressure measurement device configured to be attached to a living body. According to the present embodiment, the explanation will be given using an electronic blood pressure measurement device configured to be attached to the wrist 100 of the living body. As shown in FIGS. 1 to 12, the blood pressure measurement device 1 includes a main body 3, a strap 4, a curler 5, a cuff structure 6 including a pressing cuff 71 and a sensing cuff 73, and a fluid circuit 7. The pressing cuff 71 is one example of the cuff of the present invention.

As illustrated in FIGS. 1 to 8, the main body 3 includes a casing 11, a display 12, an operation unit 13, a pump 14, a flow passage unit 15, an on-off valve 16, a pressure sensor 17, a power supply unit 18, a vibration motor 19, and a control substrate 20. The main body 3 is a supplier that supplies fluid to the pressing cuff 71 with the pump 14, on-off valve 16, pressure sensor 17, control substrate 20 and the like.

The casing 11 includes an outer casing 31, a windshield 32 that covers the upper opening of the outer casing 31, a base 33 arranged inside the outer casing 31 at the bottom thereof, a flow passage cover 34 that covers part of the rear side of the base 33, and a back cover 35 that covers the bottom of the outer casing 31. The casing 11 further includes a flow passage tube 36 that constitutes part of the fluid circuit 7.

The outer casing 31 is cylindrically formed. The outer casing 31 includes a pair of lugs 31a arranged at each of symmetrical positions in the circumferential direction of the outer periphery, and a spring rod 31b arranged between each pair of lugs 31a. The windshield 32 is a circular glass panel.

The base 33 holds the display 12, the operation unit 13, the pump 14, the on-off valve 16, the pressure sensor 17, the power supply unit 18, the vibration motor 19 and the control substrate 20. The base 33 also constitutes part of the flow passage unit 15.

The flow passage cover 34 is fixed to the rear surface of the base 33, or in other words the outer surface thereof on the back cover 35 side. A groove is provided in either one of or both of the base 33 and flow passage cover 34, thereby constituting part of the flow passage unit 15.

The back cover 35 covers the end of the outer casing 31 on the living body side. The back cover 35 may be fixed by four screws 35a or the like to the end portion of the outer casing 31 or base 33 on the living body side.

The flow passage tube 36 constitutes part of the flow passage unit 15. The flow passage tube 36 may be coupled to the on-off valve 16 and the part of the base 33 that constitutes the flow passage unit 15.

The display 12 is arranged on the base 33 of the outer casing 31 and immediately below the windshield 32. The display 12 is electrically coupled to the control substrate 20. The display 12 may be a liquid crystal display or organic electroluminescence display. The display 12 displays various kinds of information that includes time/date and measurement results such as blood pressure values including the systolic blood pressure and diastolic blood pressure, and pulse rates.

The operation unit 13 is designed in a manner such that an instruction from a user can be input. The operation unit 13 may include a plurality of buttons 41 arranged on the casing 11, a sensor 42 configured to detect the operation of the buttons 41, and a touch panel 43 arranged on the display 12 or windshield 32. The operation unit 13 converts an instruction to an electric signal through the operation of the user. The sensor 42 and touch panel 43 are electrically coupled to the control substrate 20 so that the electric signal can be output to the control substrate 20.

The buttons 41 may include three buttons. The buttons 41 are supported by the base 33, protruding from the outer peripheral surface of the outer casing 31. The buttons 41 and sensors 42 are supported by the base 33. The touch panel 43 may be arranged integrally with the windshield 32.

The pump 14 may be a piezoelectric pump. The pump 14 compresses the air, and supplies the compressed air to the cuff structure 6 by way of the flow passage unit 15. The pump 14 is electrically coupled to the controller 55.

The flow passage unit 15 is a passage of air formed by the groove or the like provided in the main surface of the base 33 on the back cover 35 side and the flow passage cover 34 that covers the back cover 35 side of the base 33. The flow passage unit 15 constitutes the passage extending from the pump 14 to the pressing cuff 71 and the passage extending from the pump 14 to the sensing cuff 73. Furthermore, the flow passage unit 15 constitutes a passage from the pressing cuff 71 to the ambient air and a passage from the sensing cuff 73 to the ambient air. The flow passage cover 34 includes a connected portion 34a to which the pressing cuff 71 and sensing cuff 73 are coupled. The connected portion 34a may be a cylindrical nozzle provided in the flow passage cover 34.

The on-off valve 16 opens and closes part of the flow passage unit 15. The on-off valve 16 may include a plurality of valves so that the flow passage from the pump 14 to the pressing cuff 71, the flow passage from the pump 14 to the sensing cuff 73, the flow passage from the pressing cuff 71 to the ambient air and the flow passage from the sensing cuff 73 to the ambient air can be selectively opened and closed through a combination of the opening and closing of the on-off valves 16. For example, two on-off valves 16 may be adopted.

The pressure sensor 17 detects the pressures of the pressing cuff 71 and the sensing cuff 73. The pressure sensor 17 is electrically coupled to the control substrate 20. The pressure sensor 17 is electrically coupled to the control substrate 20, converts the detected pressure to an electric signal, and outputs the signal to the control substrate 20. The pressure sensor 17 may be provided in the flow passage extending from the pump 14 to the pressing cuff 71 and the flow passage extending from the pump 14 to the sensing cuff 73. These flow passages communicate with the pressing cuff 71 and the sensing cuff 73, and therefore the pressures of these flow passages are the pressures of the internal spaces of the pressing cuff 71 and the sensing cuff 73, respectively.

The power supply unit 18 may be a secondary battery such as a lithium ion battery. The power supply unit 18 is electrically coupled to the control substrate 20. The power supply unit 18 supplies power to the control substrate 20.

As illustrated in FIGS. 4 and 6, the control substrate 20 may include a substrate 51, an acceleration sensor 52, a communication unit 53, a storage 54, and a controller 55. The control substrate 20 is constituted by mounting the acceleration sensor 52, communication unit 53, storage 54 and controller 55 on the substrate 51.

The substrate 51 is fixed to the base 33 of the casing 11 with screws or the like.

The acceleration sensor 52 may be a triaxial acceleration sensor. The acceleration sensor 52 outputs to the controller 55 an acceleration signal indicating the acceleration of the main body 3 in three directions orthogonal to each other. The acceleration sensor 52 may be used for the measurement of the amount of activity of the living body wearing the blood pressure measurement device 1, based on the detected acceleration.

The communication unit 53 is configured to transmit information to, and receive information from, an external device in a wireless or wired manner. The communication unit 53 may transmit the information controlled by the controller 55 and information of the measured blood pressure value and pulse rate to the external device via a network, receive software update programs and the like from the external device via the network and send the programs to the controller.

In the present embodiment, the network may be, but is not limited to, the Internet. The network may be a local area network (LAN) provided in a hospital, or may be a form of direct communication with the external device through a cable provided with a terminal of a specific standard such as a USB. For this reason, the communication unit 53 may have multiple components including a wireless antenna and a micro USB connector.

The storage 54 stores program data for controlling the entire blood pressure measurement device 1 and the fluid circuit 7, setting data for setting various functions of the blood pressure measurement device 1, calculation data for calculating blood pressure values and pulse rate from the pressures measured by the pressure sensor 17, and the like in advance. The storage 54 also stores information including the measured blood pressure values and pulse rates.

The controller 55 is constituted by a single CPU or multiple CPUs, and controls the operation of the entire blood pressure measurement device 1 and the operation of the fluid circuit 7. The controller 55 is electrically coupled to the display 12, the operation unit 13, the pump 14, each of the on-off valves 16 and each of the pressure sensors 17, supplying power thereto.

The controller 55 further controls the operations of the display 12, the pump 14 and the on-off valves 16 based on the electric signals output by the operation unit 13 and the pressure sensors 17.

As illustrated in FIG. 4, the controller 55 may include a main CPU 56 configured to control the operation of the entire blood pressure measurement device 1 and a sub-CPU 57 configured to control the operation of the fluid circuit 7. When an instruction for the measurement of a blood pressure is input from the operation unit 13, the sub-CPU 57 may drive the pump 14 and on-off valve 16 to send the compressed air to the pressing cuff 71 and sensing cuff 73.

Furthermore, the sub-CPU 57 controls the driving and stopping of the pump 14, and opening and closing of the on-off valve 16, based on electric signals output by the pressure sensor 17 to selectively send the compressed air to the pressing cuff 71 and sensing cuff 73 and selectively depressurize the pressing cuff 71 and sensing cuff 73. From an electric signal output from the pressure sensor 17, the main CPU 56 obtains measurement results such as blood pressure values, including a systolic blood pressure and diastolic blood pressure as well as a heart rate, and outputs to the display 12 an image signal corresponding to the measurement result.

As illustrated in FIGS. 1 to 3, the strap 4 includes a first strap 61 attached to one pair of lugs 31a and a spring rod 31b, and a second strap 62 attached to the other pair of lugs 31a and the other spring rod 31b.

The first strap 61, referred to as a "main end", is shaped into a rectangle. The first strap 61 includes a first hole 61a provided in one end of the first strap 61 and extending orthogonally to the longitudinal direction of the first strap 61, a second hole 61b provided in the other end and extending orthogonally to the longitudinal direction of the first strap 61, and a buckle 61c attached to the second hole 61b. The first hole 61a has an inner diameter sufficient for the spring rod 31b to be inserted, and for the first strap 61 to rotate around the spring rod 31b. In other words, the first strap 61 is arranged between a pair of lugs 31a with the spring rod 31b inserted into the first hole 61a, thereby being rotatably supported by the outer casing 31.

The second hole 61b is provided at the tip of the first strap 61.

The buckle 61c includes a rectangular frame-shaped body 61d and a prodding stick 61e rotatably attached to the frame-shaped body 61d. One side of the frame-shaped body 61d having the prodding stick 61e is inserted into the second hole 61b, and the frame-shaped body 61d is rotatably attached to the first strap 61.

The second strap 62, referred to as a "blade end", is shaped into a rectangle having a suitable width to be inserted through the frame-shaped body 61d. The second strap 62 further includes small holes 62a through which the prodding stick 61e is inserted. The second strap 62 has a third hole 62b provided in one end and extending orthogonally to the longitudinal direction of the second strap 62. The third hole 62b is configured in a manner such that the spring rod 31b can be inserted, and has an inner diameter sufficient for the second strap 62 to rotate around the spring rod 31b. In other words, the second strap 62, which is arranged between a pair of lugs 31a with the spring rod 31b arranged in the third hole 62b, is rotatably supported by the outer casing 31. With the second strap 62 inserted through the frame-shaped body 61d and the prodding stick 61e inserted through a small hole 62a, the first strap 61 and second strap 62 are integrally connected, making the strap 4 together with the outer casing 31 into a loop to conform to the wrist 100 in the circumferential direction.

The curler 5 is formed of a resin material into a band that is bent along the circumferential direction of the wrist.

The curler 5 may have one end fixed between the base 33/flow passage cover 34 and the back cover 35 of the main body 3 and the other end in the vicinity of the main body 3. As illustrated in FIG. 5, the curler 5 may be fixed to the outer surface of the back cover 35, with one end protruding from the back cover 35 on the side of one pair of lugs 31a; and the curler 5 may protrude from the other pair of lugs 31a of the back cover 35, and extend from one end toward the other end so that the other end can be brought to a position adjacent to the one end.

A specific example is illustrated in FIGS. 1 to 3 and 12: the curler 5 may be bent along the circumferential direction of the wrist 100 when viewed in a direction perpendicular to the circumferential direction of the wrist 100, or in other words, in the side view from the longitudinal direction of the wrist 100. The curler 5 may extend from the main body 3 to the back of the wrist 100 and one lateral side of the wrist 100, to the palm side of the wrist 100, and to the other lateral side of the wrist 100. That is, the curler 5 bending along the circumferential direction of the wrist 100 surrounds most of the circumferential direction of the wrist 100, with the two ends separated while keeping a certain distance from each other.

The rigidity of the curler 5 has flexibility and shape retention. The flexibility represents deformation in the direction of the diameter of the curler 5 when an external force is applied to the curler 5. For instance, when pressed by the strap 4, the curler 5 is deformed, when viewed from the side, to become closer to the wrist, to extend along the shape of the wrist, or to conform to the shape of the wrist. The shape retention represents the capability of maintaining the original shape of the curler 5 when no external force is applied. In the present embodiment, the curler 5 maintains its curved shape along the circumferential direction of the wrist.

The curler 5 may be prepared with polypropylene to have a thickness of approximately 1 millimeter. The curler 5 supports the cuff structure 6 along the inner surface of the curler 5.

As illustrated in FIGS. 1 to 5 and 10 to 12, the cuff structure 6 includes a pressing cuff 71, a back plate 72, and a sensing cuff 73. The pressing cuff 71, back plate 72 and sensing cuff 73 are stacked and integrally formed into the cuff structure 6. The cuff structure 6 is fixed to the inner surface of the curler 5.

The pressing cuff 71 shows an exemplary cuff. The pressing cuff 71 is fluidically coupled to the pump 14 by way of the flow passage unit 15. The pressing cuff 71 is inflated to pressurize the back plate 72 and sensing cuff 73 toward the living body side. The pressing cuff 71 includes a plurality of air bags 81, a tube 82 communicating with the air bags 81, a connector 83 attached to the tip of the tube 82, and guides 84 in the air bags 81.

An air bag 81 has a bag-like structure. In the present embodiment, the blood pressure measurement device 1 is configured to send air with the pump 14, and air bags are therefore employed. If any fluid other than air is adopted, the bag-like structure may be a fluid bag for liquid or the like.

A plurality of air bags 81 are stacked together and fluidically communicate with each other in the stacking direction. Specifically, the pressing cuff 71 may include two air bags 81 fluidically communicating with each other in the stacking direction, a tube 82 at one end of one of the air bags 81 in the longitudinal direction, the connector 83 at the tip of the tube 82, and the guides 84 on the main surface of one of the two air bags 81.

In the pressing cuff 71, the main surface of the one air bag 81 is fixed to the inner surface of the curler 5. The pressing cuff 71 may be adhered to the inner surface of the curler 5 with double-sided tape or adhesive.

Each of the two air bags 81 are formed into a rectangle elongated in one direction. An air bag 81 may be formed by combining two sheet members 86 elongated in one direction to weld the edges thereof. Specifically, the two air bags 81 may include a first sheet member 86a, a second sheet member 86b forming the first air bag 81 together with the first sheet member 86a, a third sheet member 86c adhered integrally to the second sheet member 86b, a fourth sheet member 86d forming the second air bag 81 together with the third sheet member 86c, stacked in this order from the living body side, as shown in FIGS. 9 to 11.

The first sheet member 86a has a plurality of guides 84 on its outer surface on the living body side. The first sheet member 86a and second sheet member 86b form an air bag 81 with their four peripheral sides welded. The second sheet member 86b and third sheet member 86c are arranged to face each other, and include openings 86b1 and 86c1, respectively, so that the two air bags 81 can fluidically communicate with each other. An adhesive layer or double-sided tape is provided on the outer surface of the fourth sheet member 86d on the curler 5 side, and the fourth sheet member 86d is adhered to the curler 5 with this adhesive layer or double-sided tape.

The third sheet member 86c and fourth sheet member 86d form an air bag 81 with their four peripheral sides welded. Furthermore, the tube 82 may be arranged on one side of the third sheet member 86c and fourth sheet member 86d, and welded and fixed in such a manner as to fluidically communicate with the internal space of the air bag 81. The third sheet member 86c and fourth sheet member 86d form the air bag 81 by welding the four peripheral sides with the tube 82 provided between the third sheet member 86c and fourth sheet member 86d, thereby integrally adhering the tube 82.

The guides 84 may be arranged on the outer surface of the stacked air bag 81 on the living body side. When the pressing cuff 71 is inflated to pressurize the living body, the guides 84 create wrinkles on the main surface of the living body-side air bag 81 of the pressing cuff 71, or in other words in the first sheet member 86a, in a direction intersecting the winding direction of the pressing cuff 71 wound around the wrist 100.

The direction intersecting the winding direction represents a direction perpendicular or oblique with respect to the longitudinal direction of the pressing cuff 71. In order to avoid crossing of wrinkles, it is preferable that the guides 84 create wrinkles that run perpendicular to the winding direction on the living body-side main surface of the living body-side air bag 81, closer to the pressing cuff 71, when inflating the pressing cuff 71 and pressurizing the wrist.

The guides 84 are arranged on the outer surface of the first sheet member 86a of the living body-side air bag 81 of the pressing cuff 71. In other words, the guides 84 are provided in the outer surface 86a1 of the first sheet member 86a that forms, of the two air bags 81, the air bag 81 on the wrist 100 side.

The guides 84 are formed integrally with the first sheet member 86a. The guides 84 may be suitably selected and adopted from grooves, creases such as mountain fold and valley fold, and dashed-line grooves, or may be a combination of any of the aforementioned. When the guides 84 are grooves, the grooves may be formed by partially making a concave/convex pattern in the first sheet member 86a. In the case of the guides 84 being grooves, the grooves may be formed by making indented portions in the outer surface 86a1 of the first sheet member 86a. Instead of a configuration in which wrinkles are created perpendicular to the winding direction, the guides 84 may have a configuration in which grooves are inclined with respect to the winding direction or have alternating inclinations as in those of a trapezoid. The width and depth of each guide 84 may be suitably selected as long as predetermined wrinkles can be created.

The "predetermined wrinkles" are defined as having a depth that would not divide the internal space of the air bag 81 when the pressing cuff 71 is inflated to bend in accordance with the shape of the wrist 100 in the peripheral direction, and as being arranged in a manner that no overly proximate adjacent wrinkles would produce a partial pressure loss.

The width, depth, shape and configuration of each of the guides 84, and intervals of adjacent guides 84 may be suitably set as long as the predetermined wrinkles can be created. The width, depth, shape, structure and interval may be uniformly set, or may differ from each other.

According to the present embodiment, as illustrated in FIG. 9, the guides 84 are linear grooves provided in the outer surface 86a1 of the air bag 81 and extending in a direction perpendicular to the longitudinal direction of the air bag 81. Specifically, the guides 84 may be prepared by producing a concave/convex pattern in which indented portions are provided in the sheet member 86a on the side of the outer surface 86a1 and protrusions are provided on the back surface of the sheet member 86a, which is the main surface opposite the outer surface 86a1. In this manner, grooves are formed in the outer surface 86a1 of the sheet member 86a.

The guides 84 are provided on the outer surface 86a1 of the first sheet member 86a of the living body-side air bag 81 of the pressing cuff 71 in a region other than the region of the back plate 72 arranged. These guides 84 are arranged at greater intervals, where the pressing cuff 71 fixed to the curler 5 has a relatively large curvature radius, and at smaller intervals, where the pressing cuff 71 has a relatively small curvature radius.

The tube 82 is coupled to one of the two air bags 81, and is arranged at one end of this air bag 81 in the longitudinal direction. Specifically, the tube 82 may be arranged, of the two air bags 81, in the air bag 81 on the curler 5 side and at the end thereof close to the main body 3. The tube 82 has a connector 83 at its tip end. The tube 82 constitutes, of the fluid circuit 7, the flow passage between the main body 3 and the air bag 81. The connector 83 is coupled to the connected portion 34a of the flow passage cover 34. The connector 83 may be a nipple.

The back plate 72 is adhered to the outer surface 86a1 of the first sheet member 86a of the pressing cuff 71 with an adhesive layer or double-sided tape. The back plate 72 may be formed of a resin material into a plate. The back plate 72 may be formed of polypropylene into a plate approximately 1 millimeter thick. The back plate 72 has a shape-conforming capability.

The shape-conforming capability represents the deformability of the back plate 72 that can conform to the shape of the contact portion of the wrist 100. The contact portion of the wrist 100 represents the portion brought into contact with the back plate 72, and this contact may be direct contact or indirect contact.

In view of this, with the shape-conforming capability, the back plate 72 may be deformed in a manner such that the back plate 72 or the sensing cuff 73 arranged on the back plate 72 conforms to the shape of the wrist 100, or may be deformed to conform to the shape of the wrist 100 until it substantially fits the wrist 100. Here, the back plate 72 may be provided in the pressing cuff 71 or between the pressing cuff 71 and the sensing cuff 73.

The back plate 72 may have a plurality of grooves 72a at facing positions on the two main surfaces of the back plate 72, at regular intervals in the longitudinal direction of the back plate 72. As a result, the back plate 72 is thinner in the portion where the grooves 72a are provided than in the portion where the grooves 72a are not provided, making the portions with the grooves 72a easily deformable. The back plate 72 thereby demonstrates the shape-conforming capability of deforming in accordance with the shape of the wrist 100. The back plate 72 is designed to have a length sufficient to cover the palm side of the wrist 100.

The back plate 72, when being in the state of conforming to the shape of the wrist 100, conveys the pressing force from the pressing cuff 71 to the main surface of the sensing cuff 73 on the back plate 72 side.

The sensing cuff 73 is fixed to the main surface of the back plate 72 on the living body side. The sensing cuff 73 is brought into direct contact with the area of the wrist 100 where the arteries run, as illustrated in FIG. 12. The sensing cuff 73 is formed to have the same shape as the back plate 72 or to be smaller than the back plate 72 in the longitudinal direction and width direction of the back plate 72. The sensing cuff 73 is inflated to pressurize an artery 110 on the palm side of the wrist 100. The sensing cuff 73 is pressurized toward the living body side by the inflated pressing cuff 71 with the back plate 72 interposed between.

Specifically, the sensing cuff 73 may include one air bag 91, a tube 92 communicating with the air bag 91, and a connector 93 provided at the tip of the tube 92. In the sensing cuff 73, one of the main surfaces of the air bag 91 is fixed to the back plate 72. The sensing cuff 73 may be adhered to the living body-side main surface of the back plate 72 with double-sided tape or an adhesive layer.

The air bag 91 has a bag-like structure. In the present embodiment, the blood pressure measurement device 1 is configured to send air with the pump 14, and therefore air bags are employed. If any fluid other than air is adopted, the bag-like structure may be a fluid bag for liquid or the like.

The air bag 91 is formed into a rectangle elongated in one direction. The air bag 91 may be prepared by combining two sheet members elongated in one direction and welding their edges. Specifically, the air bag 91 may include a fifth sheet member 96a and a sixth sheet member 96b arranged in this order from the living body side, as illustrated in FIGS. 9 and 10.

A tube 92 may be arranged on one side of the fifth sheet member 96a and the sixth sheet member 96b in such a manner as to fluidically communicate with the internal space of the air bag 91, and the fifth sheet member 96a and sixth sheet member 96b may be welded with the tube 92 fixed. The tube 92 may be integrally adhered through the formation of the air bag 91 by welding the four edges of the fifth sheet member 96a and the sixth sheet member 96b with the tube 92 between the fifth sheet member 96a and the sixth sheet member 96b.

The tube 92 is attached to one end of the air bag 91 in the longitudinal direction. Specifically, the tube 92 is attached to the end of the air bag 91 closer to the main body 3. The tube 92 has a connector 93 at its tip. The tube 92 constitutes, of the fluid circuit 7, a flow passage between the main body 3 and the air bag 91. The connector 93 is coupled to the connected portion 34a of the flow passage cover 34. The connector 93 may be a nipple.

The sheet members 86 and 96 that form the pressing cuff 71 and sensing cuff 73 are prepared with a thermoplastic elastomer. The thermoplastic elastomer for the sheet members 86 and 96 may be thermoplastic polyurethane (hereinafter, "TPU") resin, polyvinyl chloride resin, ethylene-vinyl acetate resin, thermoplastic polystyrene resin, thermoplastic polyolefin resin, thermoplastic polyester resin or thermoplastic polyamide resin. As the thermoplastic elastomer, the use of TPU is preferable. The sheet material may have a monolayered structure or multi-layered structure.

The sheet members 86 and 96 are not limited to thermoplastic elastomer but may be a thermoset elastomer such as silicone. They may be a combination of a thermoplastic elastomer (such as TPU) and a thermoset elastomer (such as silicone).

When a thermoplastic elastomer is adopted, the sheet members 86b, 86c, 86d and 96 that do not include guides 84 are shaped with a forming technique such as T-die extrusion, injection, blow molding and calendaring. When a thermoset elastomer is adopted, a forming technique such as mold casting is used.

For a sheet member 86a that includes guides 84, when a thermoplastic elastomer is adopted, a forming technique such as profile extrusion and injection may be used for formation of a sheet having a concave/convex pattern that serves as grooves or guides 84 in the resin material. Alternatively, a forming technique such as embossing, thermal pressing, vacuum forming and pressure forming may be used for producing a concave/convex pattern that serves as grooves or the guides 84 in the flat sheet. When a thermoset elastomer is adopted, a forming technique such as mold casting that uses a mold to which a concave/convex pattern is provided as grooves or the guides 84 may be adopted for the sheet member 86a including guides 84.

The sheet members 86 and 96 are formed with a forming technique and thereafter sized into a predetermined shape. The sized pieces are bonded through adhesion or welding to form air bags 81 and 91. As a bonding technique, when a thermoplastic elastomer is adopted, high frequency welding or laser welding is used. When a thermoset elastomer is adopted, a molecular adhesive is used.

The fluid circuit 7 is constituted by a casing 11, a pump 14, a flow passage unit 15, on-off valves 16, pressure sensors 17, a pressing cuff 71 and a sensing cuff 73. The on-off valves 16 of the fluid circuit 7 may include two valves, namely a first on-off valve 16A and a second on-off valve 16B, and the pressure sensors 17 may include two sensors, namely a first pressure sensor 17A and a second pressure sensor 17B. An exemplary fluid circuit 7 will be explained below.

As illustrated in FIG. 4, the fluid circuit 7 may include a first flow passage 7a making the pump 14 continuous to the pressing cuff 71, a second flow passage 7b branching from the middle portion of the first flow passage 7a and making the pump 14 continuous to the sensing cuff 73, and a third flow passage 7c connecting the first flow passage 7a with ambient air. The first flow passage 7a includes the first pressure sensor 17A. The first on-off valve 16A is arranged between the first flow passage 7a and the second flow passage 7b. The second flow passage 7b includes the second pressure sensor 17B. The second on-off valve 16B is arranged between the first flow passage 7a and the third flow passage 7c.

In this fluid circuit 7, only the first flow passage 7a is connected to the pump 14 by closing the first on-off valve 16A and the second on-off valve 16B so that the pump 14 and the pressing cuff 71 can be fluidically connected to each other. Furthermore, in the fluid circuit 7, the first flow passage 7a and the second flow passage 7b are connected to each other by opening the first on-off valve 16A and closing the second on-off valve 16B so that the pump 14 and the pressing cuff 71 can be fluidically connected to each other, and the pump 14 and the sensing cuff 73 can also be fluidically connected to each other. In the fluid circuit 7, the first flow passage 7a and the third flow passage 7c are connected to each other by closing the first on-off valve 16A and the second on-off valve 16B so that the pressing cuff 71 can be fluidically connected to ambient air. In the fluid circuit 7, the first flow passage 7a, second flow passage 7b and third flow passage 7c are connected to each other by opening the first on-off valve 16A and the second on-off valve 16B so that the pressing cuff 71 and sensing cuff 73 can be fluidically connected to ambient air.

Figure 15:
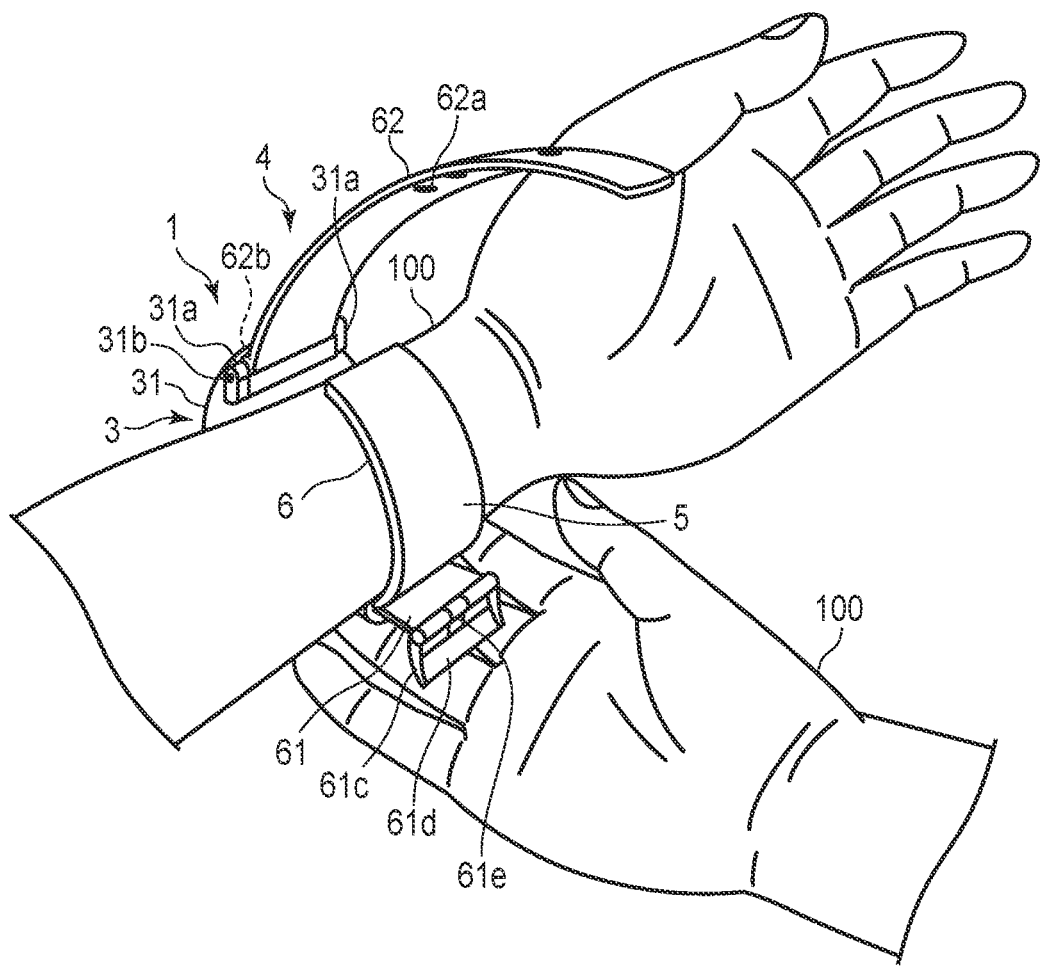
FIG. 15 is a perspective view of the blood pressure measurement device when being attached around the wrist.
Figure 16:
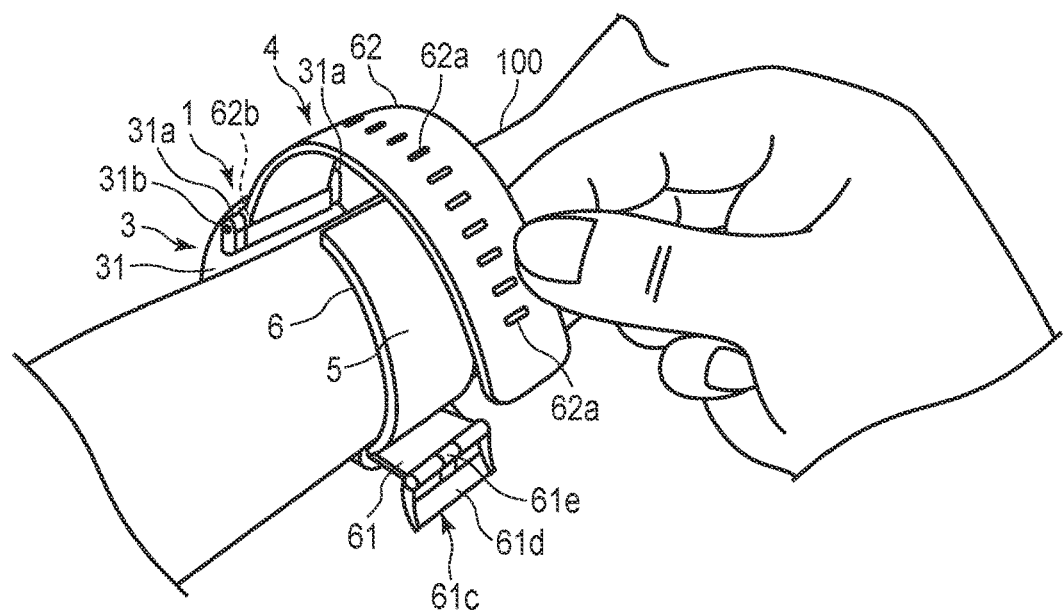
FIG. 16 is a perspective view showing an example of the blood pressure measurement device being attached around the wrist.
Figure 17:
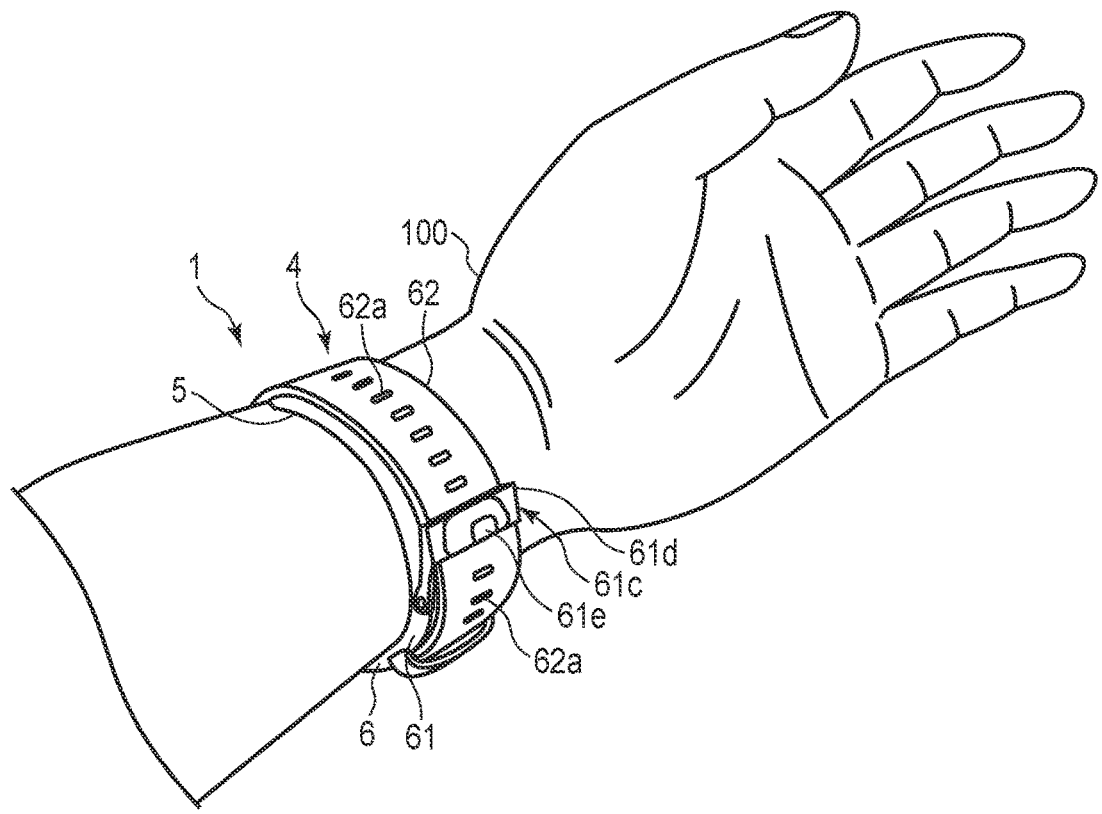
FIG. 17 is a perspective view showing an example of the blood pressure measurement device being attached around the wrist.

Next, an exemplary measurement of a blood pressure value through the use of the blood pressure measurement device 1 will be explained with reference to FIGS. 14 to 17. FIG. 14 is a flowchart of the exemplary blood pressure measurement with the blood pressure measurement device 1, which includes both the user's operation and the operation of the controller 55. FIGS. 15 to 17 show an example of the user wearing the blood pressure measurement device 1 around the wrist 100.

First, the user attaches the blood pressure measurement device 1 around the wrist 100 (step ST1). Specifically, the user may place the wrist 100 into the curler 5, as illustrated in FIG. 15.

At this stage, the main body 3 and sensing cuff 73 of the blood pressure measurement device 1 are placed at positions of the curler 5 that face each other, and therefore the sensing cuff 73 can be placed on the palm side of the wrist 100 where the artery 110 runs. This means that the main body 3 is placed on the back side of the wrist 100. Thereafter, the user threads the second strap 62 through the frame-shaped body 61d of the buckle 61c of the first strap 61 with the hand to which the blood pressure measurement device 1 is not attached, as illustrated in FIG. 16. Then, the user pulls the second strap 62 to tighten the part provided on the inner surface of the curler 5, or in other words the cuff structure 6, onto the wrist 100, and threads the prodding stick 61e into a small hole 62a. In this manner, as illustrated in FIG. 17, the first strap 61 and second strap 62 are connected to each other, and the blood pressure measurement device 1 is attached around the wrist 100.

Next, the user manipulates the operation unit 13 to input an instruction corresponding to the initiation of the blood pressure measurement. The operation unit 13, on which the instruction input operation is performed, outputs an electric signal corresponding to the initiation of the measurement to the controller 55 (step ST2). Upon the receipt of this electric signal, the controller 55 may open the first on-off valve 16A and close the second on-off valve 16B, and drive the pump 14 to supply compressed air to the pressing cuff 71 and sensing cuff 73 through the first flow passage 7a and second flow passage 7b (step ST3). This initiates the inflation of the pressing cuff 71 and sensing cuff 73.

The first pressure sensor 17A and second pressure sensor 17B detect the pressures of the pressing cuff 71 and sensing cuff 73, respectively, and outputs electric signals corresponding to these pressures to the controller 55 (step ST4). Based on the received electric signals, the controller 55 determines whether or not the pressures of the internal space of the pressing cuff 71 and sensing cuff 73 have reached the predetermined pressures for the blood pressure measurement (step ST5). For instance, if the internal pressure of the pressing cuff 71 has not reached its predetermined pressure while the internal pressure of the sensing cuff 73 has reached its predetermined pressure, the controller 55 closes the first on-off valve 16A to supply the compressed air through the first flow passage 7a.

When the internal pressure of the pressing cuff 71 and the internal pressure of the sensing cuff 73 both reach their corresponding predetermined pressures, the controller 55 stops driving the pump 14 ("yes" at step ST5). In this case, the pressing cuff 71 has been sufficiently inflated as illustrated in FIG. 12, and the inflated pressing cuff 71 thereby presses the wrist 100 and the back plate 72. Furthermore, the pressing cuff 71 has wrinkles created along the guides 84.

The sensing cuff 73 is inflated with a predetermined amount of air supplied in order to bring the internal pressure of the sensing cuff 73 to a pressure level required for the measurement of the blood pressure. The sensing cuff 73 is thereby pressed toward the wrist 100 by the back plate 72 that is pressed by the pressing cuff 71. As a result, the sensing cuff 73 pressurizes the artery 110 in the wrist 100 and blocks the artery 110, as illustrated in FIG. 13.

Furthermore, the controller 55 controls the second on-off valve 16B to repeat the opening and closing of the second on-off valve 16B or to adjust the degree of opening of the second on-off valve 16B, thereby increasing the pressure of the internal space of the pressing cuff 71. Based on the electric signal output by the second pressure sensor 17B in this process, the controller 55 acquires the results of the measurement such as blood pressure values including the systolic and diastolic blood pressures, and heart rate.

In the above explained example, the timings of opening and closing the first on-off valve 16A and the second on-off valve 16B at the time of blood pressure measurement can be suitably set, and the controller 55 calculates the blood pressure during the process of pressurizing the pressing cuff 71. The blood pressure, however, may be calculated during the process of depressurizing the pressing cuff 71 or during both the processes of pressurizing and depressurizing the pressing cuff 71. Thereafter, the controller 55 outputs an image signal corresponding to the acquired measurement result to the display 12.

Upon receipt of the image signal, the display 12 displays the measurement result on the screen. The user views the display 12 and thereby ascertains the measurement result. When the measurement is completed, the user removes the prodding stick 61e from the small holes 62a, the second strap 62 from the frame-shaped body 61d, and the wrist 100 from the curler 5, thereby removing the blood pressure measurement device 1 from the wrist 100.

In the blood pressure measurement device 1 having the above structure according to the present embodiment, guides 84 are provided for creating wrinkles in the outer surface of the pressing cuff 71 of the cuff structure 6 on the living body side. With such a configuration, when the pressing cuff 71 of the cuff structure 6 on the inner surface of the curler 5 is inflated, wrinkles can be created at predetermined positions of the pressing cuff 71 on the living body side. In this manner, the accuracy of the measurement result of the measured blood pressure can be improved in the blood pressure measurement device 1.

This effect is explained in detail below. The curler 5 of the blood pressure measurement device 1 is shaped to extend along the circumferential direction of the wrist 100, and therefore the pressing cuff 71 is shaped to bend with a predetermined curvature. When the pressing cuff 71 is inflated, the difference in the curvature radius between the inner peripheral surface and the outer peripheral surface creates a difference in the peripheral length of the inflated pressing cuff 71 between the inner peripheral surface and the outer peripheral surface, which is an inner/outer peripheral difference. With this inner/outer peripheral difference, the inner peripheral surface of the pressing cuff 71 is bent at some portions, creating wrinkles toward the outer peripheral surface in the radial direction. The created wrinkles tend to have a larger depth at portions with a smaller curvature radius.

The wrinkles may cause, depending on their positions and depths, division of the internal space of the pressing cuff 71 or a loss in the inflating pressure. In other words, the wrinkles created in the inner peripheral surface of the pressing cuff 71 may become a factor of adverse effects on the measurement result of the blood pressure, such as reduction in the accuracy of the blood pressure measurement and variation in measurement results.

In the blood pressure measurement device 1 according to the present embodiment, the main body 3 and the sensing cuff 73 are arranged at the positions facing each other across the curler 5. For this reason, if a deep wrinkle is created in the pressing cuff 71 in the middle of the portion stretching from the main body 3 to the sensing cuff 73, the wrinkle may divide the internal space of the pressing cuff 71 or cause a pressure loss. If this is the case, the pressure inside the region of the pressing cuff 71 configured to pressurize the sensing cuff 73 would not increase to reach the predetermined pressure, preventing an accurate value from being acquired as the blood pressure measurement result.

According to the present embodiment, the guides 84 are provided in the pressing cuff 71 as described above to serve as starting points of wrinkling when the pressing cuff 71 is inflated and an inner/outer peripheral difference appears between the inner peripheral surface and outer peripheral surface of the pressing cuff 71. Thus, the wrinkles can be formed from the guides 84 as the starting points. By providing a predetermined number of guides 84, the positions and depths of wrinkles, which are generally caused by the inner/outer peripheral difference, can be controlled. Furthermore, even when the conditions of use of the blood pressure measurement device 1 vary, or when the thickness of the wrist 100 varies depending on the user, the numbers and depths of wrinkles are still controllable with the arrangement of the guides 84. Thus, fluctuations in the blood pressure measurement results can be avoided at the blood pressure measurement, and the accuracy of the blood pressure measurement result can be improved.

In addition, the guides 84 are provided in an area of the pressing cuff 71 or the like, other than that where the sensing cuff 73 is arranged, or in other words in an area that does not include the position facing the artery. In this manner, the formation of wrinkles, which generally occurs through inner/outer peripheral difference, can be suppressed in the area where the sensing cuff 73 is arranged.

As a result, the pressing cuff 71 can pressurize the back plate 72 of the sensing cuff 73 with its bent surface, thus uniformly pressurizing the sensing cuff 73. In this manner, formation of wrinkles in the sensing cuff 73 can be avoided, and the sensing cuff 73 can suitably pressurize the artery 110.

Moreover, grooves are provided as the guides 84 in the outer surface 86a1 of the sheet member 86a in accordance with the concave/convex pattern formed in the sheet member 86a of the pressing cuff 71. Thus, the pressing cuff 71 can be formed to have a uniform thickness without increasing or decreasing the thickness of the sheet member 86a, and the control of wrinkles can be realized with a simple structure. In addition, the guides 84 can be formed in the first sheet member 86a that constitutes the pressing cuff 71, at the time of forming the first sheet member 86a or pressing cuff 71. This facilitates the manufacturing of the pressing cuff 71.

As described above, in the blood pressure measurement device 1 according to the first embodiment, guides 84 are provided for formation of wrinkles on the main surface of the pressing cuff 71 on the living body side. Thus, a desired number of wrinkles can be created at desired positions, thereby improving the accuracy of the blood pressure measurement result.

In the present embodiment, the main body 3 is arranged on the back side of the wrist 100; however, the main body 3 may be arranged on the palm side of the wrist 100. That is, the main body 3 may be fixed to the outer surface of the curler 5 where the sensing cuff 73 is arranged. The blood pressure measurement device 1 of such a structure can be arranged in the area where the artery of the wrist 100 runs with the main body 3 arranged on the palm side. This reduces the distance to the sensing cuff 73, which shortens the length of the tube 92 attached to the sensing cuff 73.

Second Embodiment

The pressing cuff 71A in the second embodiment will be explained with reference to FIGS. 18 and 19. The second embodiment differs from the blood pressure measurement device 1 according to the first embodiment in the pressing cuff adopted in the cuff structure 6, and therefore the structure other than the pressing cuff will be omitted from the explanation. In the present embodiment, the same numerals are used for the same structural components as those of the blood pressure measurement device 1 according to the first embodiment, and the detailed explanation thereof is omitted.

Figure 18:
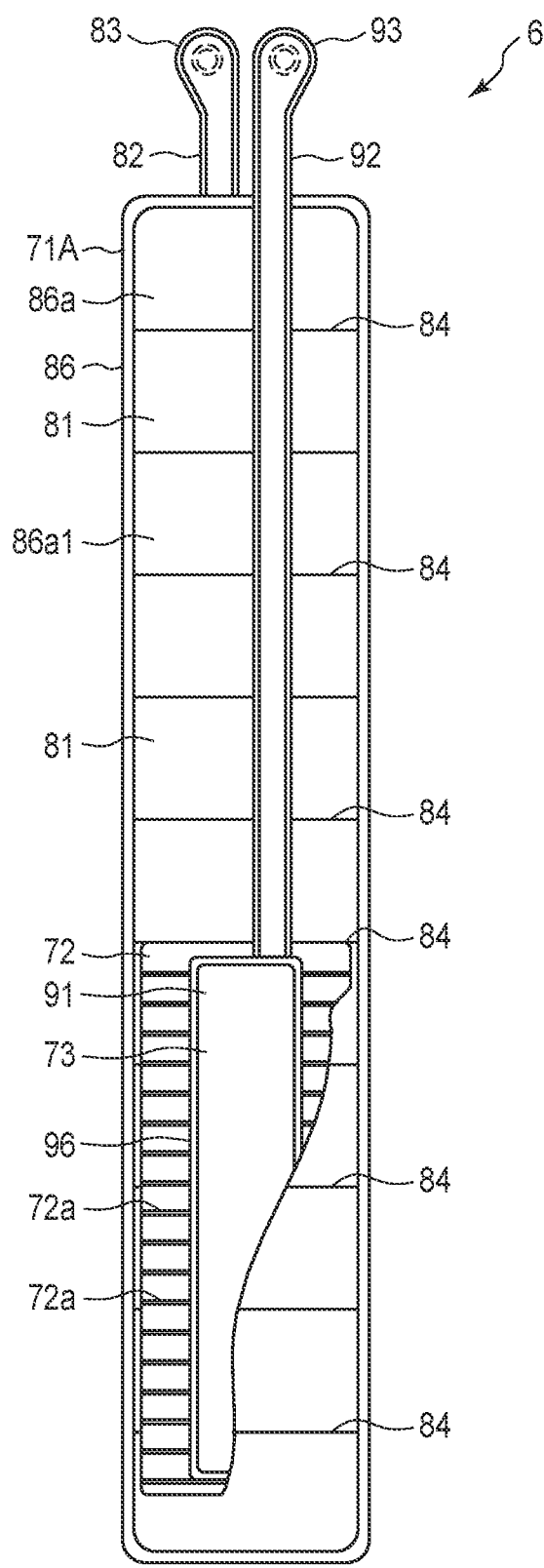
FIG. 18 is a plan view showing the configuration of a cuff structure according to the second embodiment of the present invention.
Figure 19:
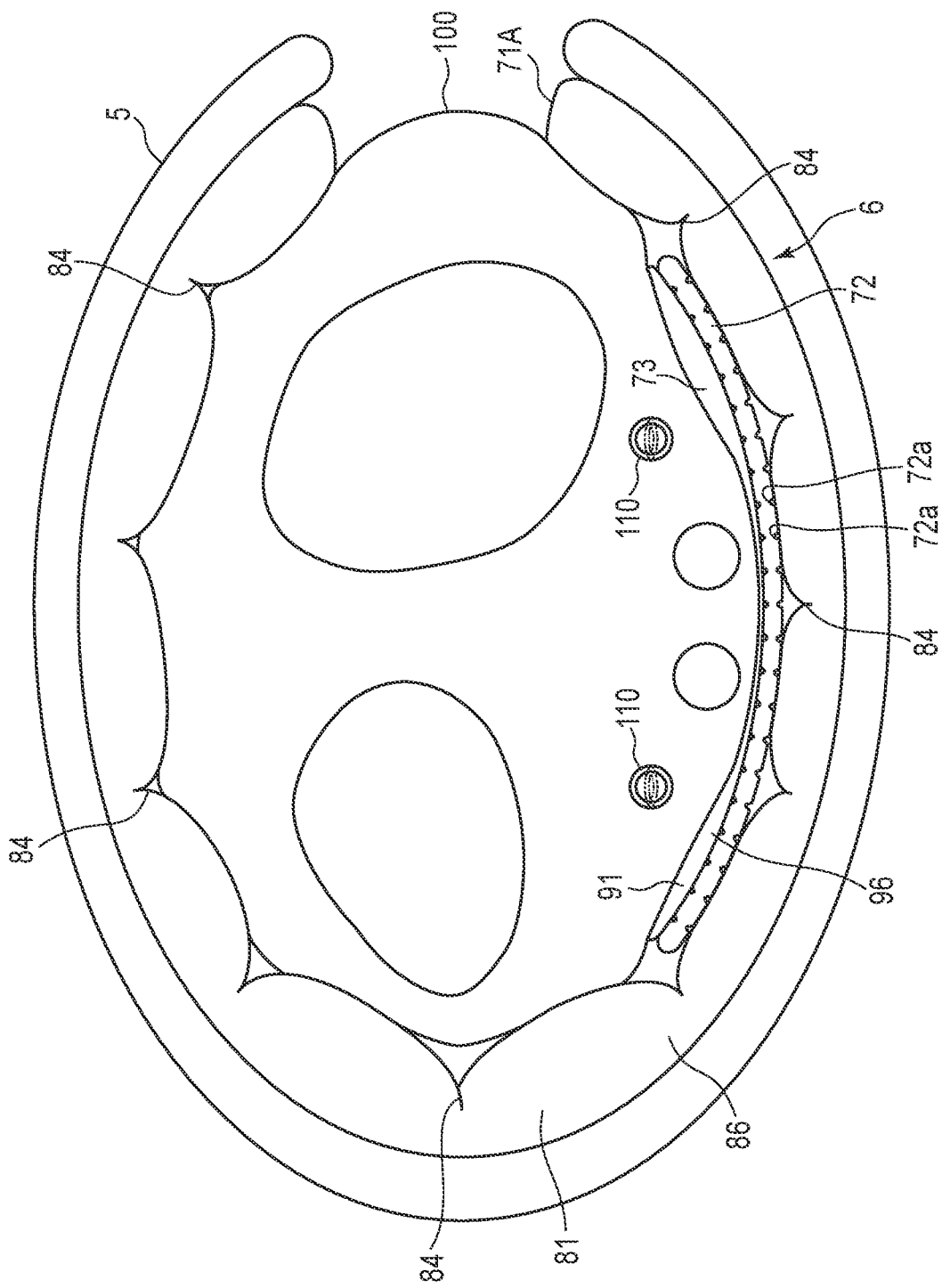
FIG. 19 is a side view schematically showing the configuration of the pressing cuff of the cuff structure when inflated.

FIG. 18 is a plan view for schematically showing the structure of the pressing cuff 71A according to the second embodiment, and FIG. 19 is a side view for schematically showing the structure of the blood pressure measurement device 1 adopting the pressing cuff 71A, when inflated.

As illustrated in FIG. 18, a plurality of guides 84 are provided at regular intervals in the pressing cuff 71A. In such a pressing cuff 71A, the guides 84 may be arranged at intervals of 15 millimeters.

Such a pressing cuff 71A, when inflated, has wrinkles at regular intervals as illustrated in FIG. 19, and the wrinkles can be formed to have a depth as uniform as possible.

In this manner, the internal space of the pressing cuff 71A can be prevented from partially cleaving, and the pressing cuff 71A can uniformly pressurize the back plate 72 without any loss of the inflating pressure. Thus, in the same manner as the above-mentioned pressing cuff 71, the accuracy of the blood pressure measurement result can be improved.

Third Embodiment

Next, the pressing cuff 71B according to the third embodiment will be explained with reference to FIGS. 20 and 21.

The third embodiment differs from the above-mentioned blood pressure measurement device 1 according to the first embodiment only in the structure of the pressing cuff adopted in the cuff structure 6, and therefore the structure other than the pressing cuff will be omitted from the explanation. Furthermore, in the present embodiment, the same numerals are used for the same structural components as those of the blood pressure measurement device 1 according to the first embodiment, and the detailed explanation thereof is omitted.

Figure 20:
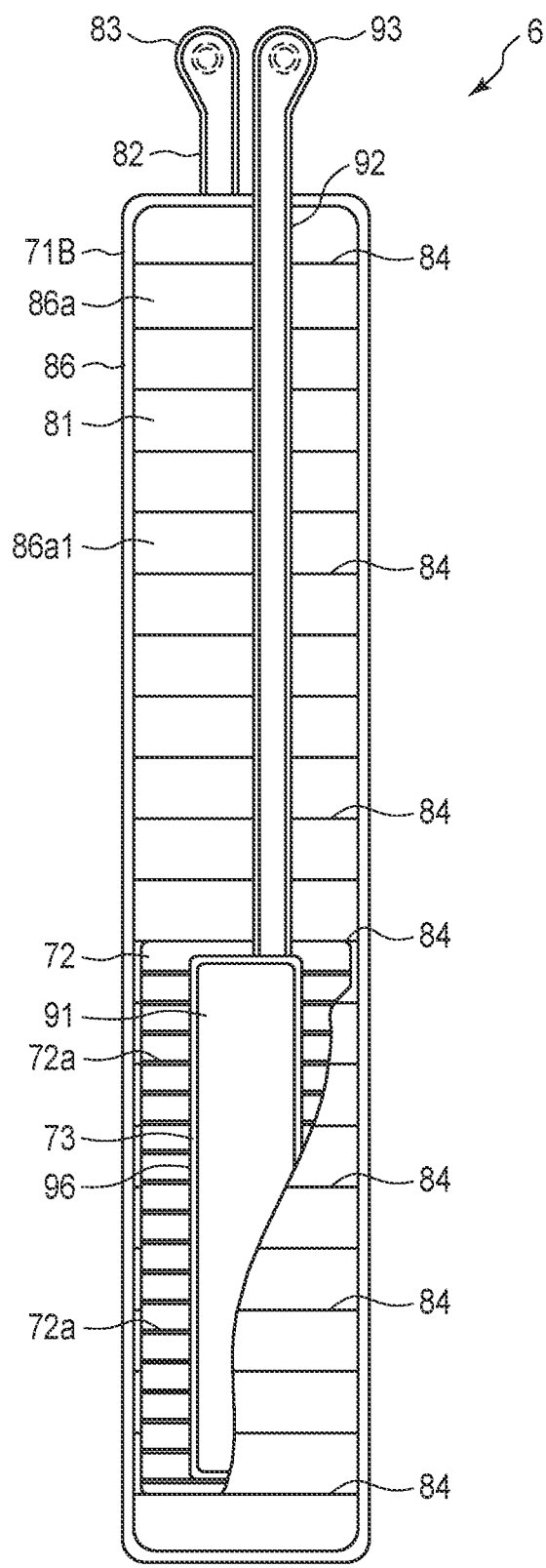
FIG. 20 is a plan view showing the configuration of the cuff structure according to the third embodiment of the present invention.
Figure 21:
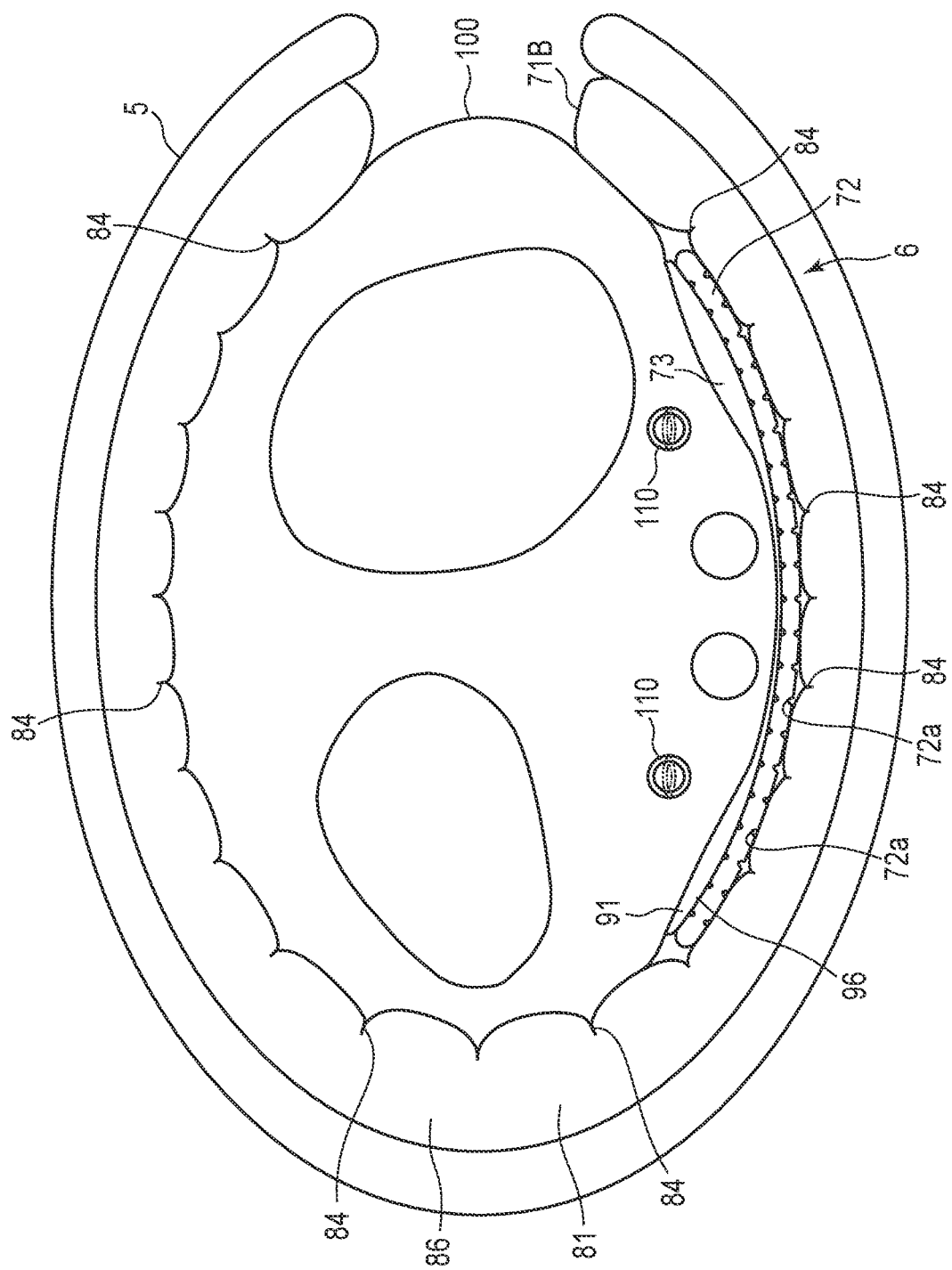
FIG. 21 is a side view schematically showing the configuration of the pressing cuff of the cuff structure when inflated.

FIG. 20 is a plan view for schematically showing the structure of the pressing cuff 71B according to the third embodiment, and FIG. 21 is a side view for schematically showing the structure of the blood pressure measurement device 1 adopting the pressing cuff 71B, when inflated.

As illustrated in FIG. 20, a plurality of guides 84 are provided at regular intervals in the pressing cuff 71B. In such a pressing cuff 71B, the guides 84 are arranged at intervals of 5 millimeters.

Such a pressing cuff 71B, when inflated, has wrinkles at regular intervals as illustrated in FIG. 21, and the wrinkles can be formed to have a depth as uniform as possible. Furthermore, the guides 84 are arranged at smaller intervals and of a larger number in the pressing cuff 71B than in the aforementioned pressing cuff 71A. Thus, more wrinkles can be formed by the guides 84 than in the pressing cuff 71A.

With the arrangement of a large number of guides 84, the wrinkles in the pressing cuff 71B can be formed to be shallow. The wrinkles are created due to an inner/outer peripheral difference, and therefore the sum of the depths of the wrinkles created due to the inner/outer peripheral difference is approximately constant. This means that more wrinkles have smaller depths. As a result, the internal space of the pressing cuff 71B can be prevented from partially cleaving, and the back plate 72 can be uniformly pressurized without a loss of the inflating pressure. In the same manner as the pressing cuffs 71 and 71A, the accuracy of the blood pressure measurement result can be improved.

Fourth Embodiment

Next, the pressing cuff 71 according to the fourth embodiment will be explained with reference to FIGS. 22 to 24.

In the fourth embodiment, a blood pressure measurement device 10 that is wound around the upper arm to measure the blood pressure and that uses a cuff including guides 84 is adopted in place of the blood pressure measurement device 1 for the wrist 100 according to the first embodiment. The same numerals are assigned to the same components as those of the blood pressure measurement device 1 according to the first embodiment, and the explanation and illustration will be omitted as needed.

Figure 22:
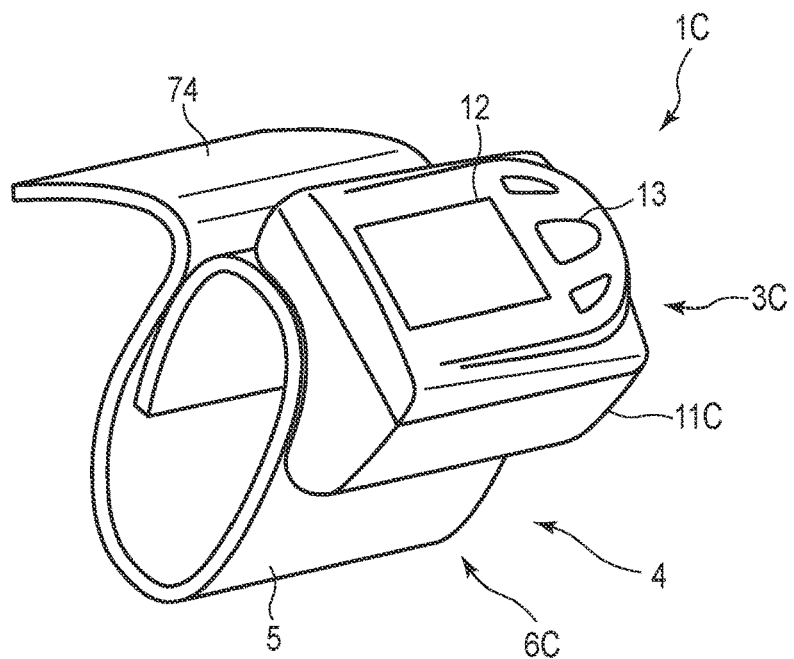
FIG. 22 is a perspective view showing the configuration of the blood pressure measurement device according to the fourth embodiment.
Figure 23:
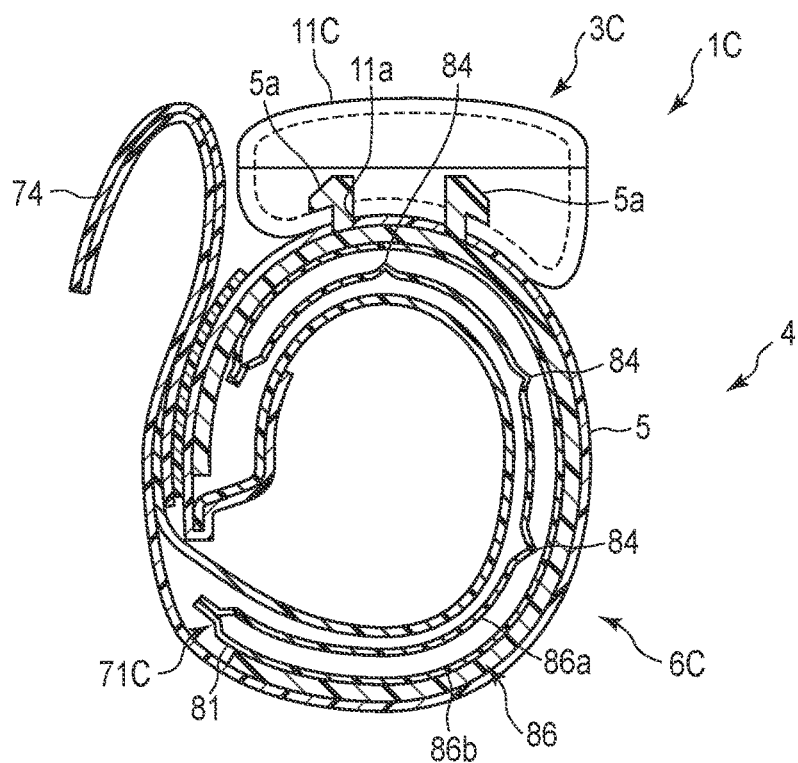
FIG. 23 is a cross-sectional view showing the configuration of the blood pressure measurement device.

As illustrated in FIGS. 22 to 24, the blood pressure measurement device 10 according to the fourth embodiment may include a main body 3C and a cuff structure 6C. The main body 3C may include a casing 11C, a display 12, an operation unit 13, a pump 14, a flow passage unit 15, an on-off valve 16, a pressure sensor 17, a power supply unit 18, and a control substrate 20. As illustrated in FIG. 24, the main body 3C includes a pump 14, an on-off valve 16 and a pressure sensor 17.

The casing 11C may be shaped into a box. The casing 11C includes an attachment portion 11a for the fixation of the cuff structure 6C. The attachment portion 11a may be an opening in the rear surface of the casing 11C.

As illustrated in FIGS. 22 to 24, the cuff structure 6C includes a curler 5, a pressing cuff 71C on the living body side of the curler 5, and a bag-like cover 74 formed of fabric or the like for holding the curler 5 and the pressing cuff 71C inside. The cuff structure 6C is designed to be wound around the upper arm.

The curler 5 may have protrusions 5a so as to be fixed to the attachment portion 11a.

The pressing cuff 71C includes an air bag 81 and guides 84 in one of the main surfaces of the air bag 81. In other words, the pressing cuff 71C has a configuration of one air bag 81 having the guides 84.

The pressing cuff 71C is contained together with the curler 5 in the bag-like cover 74, and fixed to the inner surface of the curler 5. The pressing cuff 71C may be adhered to the inner surface of the curler 5 with double-sided tape or an adhesive.

The air bag 81 is formed as a rectangle having longer sides in one direction. The air bag 81 may be prepared by combining two sheet members 86 having longer sides in one direction and welding their edges. Specifically, the air bag 81 may include a first sheet member 86a, and a second sheet member 86b that constitutes the air bag 81 together with the first sheet member 86a in this order from the living body side, as illustrated in FIG. 23. The first sheet member 86a has a plurality of, guides 84 on its outer surface on the living body side.

In the same manner as the aforementioned blood pressure measurement device 1, the blood pressure measurement device 1C having the above configuration can control the number and positions of wrinkles created due to the inner/outer peripheral difference by providing the guides 84 in the inner surface of the pressing cuff 71C on the living body side. Thus, part of the internal space of the pressing cuff 71C can be prevented from cleaving, and the pressing cuff 71C can uniformly pressurize the upper arm without a loss in the inflating pressure. Thus, in the same manner as the pressing cuff 71, the accuracy of the blood pressure measurement result can be improved. As discussed above, even in the configuration in which the cuff structure 6C is designed to be wound around the upper arm, the blood pressure measurement device 1C having a pressing cuff 71C with the guides 84 can improve the accuracy of the blood pressure measurement result.

The above embodiments are described merely as examples of the present invention in any aspect. Various improvements and modifications can be made without departing the scope of the invention. A specific structure corresponding to the embodiment may be suitably adopted when the invention is carried out.

1 Blood pressure measurement device
1C Blood pressure measurement device
3 Main body
3C Main body
4 Strap
5 Curler
5a Protrusion
6 Cuff structure
6C Cuff structure
7 Fluid circuit
7a First flow passage
7b Second flow passage
7c Third flow passage
11 Casing
11a Attachment portion
11C Casing
12 Display
13 Operation unit
14 Pump
15 Flow passage unit
16 On-off valve
16A First on-off valve
16B Second on-off valve
17 Pressure sensor
17A First pressure sensor
17B Second pressure sensor
18 Power supply unit
19 Vibration motor
20 Control substrate
31 Outer casing
31a Lug
31b Spring rod
32 Windshield
33 Base
34 Flow passage cover
34a Connected portion
35 Back cover
35a Screw
36 Flow passage tube
41 Button
42 Sensor
43 Touch panel
51 Substrate
52 Acceleration sensor
53 Communication unit
54 Storage
55 Controller
61 First strap
61a First hole
61b Second hole
61c Buckle
61d Frame-shaped body
61e Prodding stick
62 Second strap
62a Small hole
71 Pressing cuff
71A Pressing cuff
71B Pressing cuff
71C Pressing cuff
72 Back plate
72a Groove
73 Sensing cuff
74 Bag-like cover
81 Air bag
82 Tube
83 Connector
84 Guide
86 Sheet member
86a First sheet member
86a1 Outer surface
86b Second sheet member
86b1 Opening
86c Third sheet member
86c1 Opening
86d Fourth sheet member
91 Bag-like structure
91 Air bag
92 Tube
93 Connector
96 Sheet member
96a Fifth sheet member
96b Sixth sheet member
100 Wrist
110 Artery

The invention claimed is:

1. A blood pressure measurement device comprising:
a bag-like pressing cuff formed by a plurality of sheet members and configured to be wound around a living body and inflated with a fluid supplied to internal space thereof, the pressing cuff being shaped in a rectangle elongated in a longitudinal direction of the pressing cuff with four peripheral sides of each of the sheet members being respectively welded together;
a supply device configured to supply the fluid into the pressing cuff;
guides arranged in the pressing cuff on a living body side and configured to create wrinkles in the pressing cuff on the living body side at positions of the guides, in a direction intersecting a winding direction of the pressing cuff, only when the pressing cuff is inflated to pressurize the living body;

a back plate arranged on the living body side of the pressing cuff and extending in a circumferential direction of a measurement target site of the living body;

a bag-like sensing cuff arranged on the living body side of the back plate, arranged in an area of the measurement target site where an artery runs when the pressing cuff is wound around the living body, and inflated with the fluid supplied to the internal space;

a main body that includes a pump configured to supply the fluid to the pressing cuff and the sensing cuff and serves as the supply device; and a strap arranged on the main body in such a manner as to be attached to the measurement target site along the circumferential direction thereof, wherein the guides are a plurality of grooves arranged in an outer surface of only one of the sheet members arranged on the living body side, with no guides being arranged in the sensing cuff, and the guides are arranged at regular intervals in an entire area of the pressing cuff in the longitudinal direction of the pressing cuff, the entire area extending between first and second free ends of the pressing cuff such that the guides are arranged at the regular intervals continuously between the first and second free ends of the pressing cuff.

2. The blood pressure measurement device according to claim 1, wherein the guides create the wrinkles in a direction perpendicular to the winding direction of the pressing cuff.

* * * * *